(12) United States Patent
Qi et al.

(10) Patent No.: US 10,806,145 B2
(45) Date of Patent: Oct. 20, 2020

(54) APPLICATIONS OF PROTEIN VDAL IN IMPROVING OUTPUT, PRODUCT QUALITY AND DROUGHT RESISTANCE OF PLANT AND IN IMPROVING FRUIT COLORING OF PLANT

(71) Applicant: PHEROBIO TECHNOLOGY CO., LTD, Beijing (CN)

(72) Inventors: Junsheng Qi, Beijing (CN); Zhizhong Gong, Beijing (CN); Xuhui Hong, Beijing (CN); Dingpeng Zhang, Beijing (CN)

(73) Assignee: PHEROBIO TECHNOLOGY CO., LTD, Beijing (CN)

( * ) Notice: Subject to any disclaimer, the term of this patent is extended or adjusted under 35 U.S.C. 154(b) by 195 days.

(21) Appl. No.: 15/769,746

(22) PCT Filed: Jul. 1, 2016

(86) PCT No.: PCT/CN2016/088074
§ 371 (c)(1),
(2) Date: Apr. 20, 2018

(87) PCT Pub. No.: WO2017/067214
PCT Pub. Date: Apr. 27, 2017

(65) Prior Publication Data
US 2018/0235229 A1 Aug. 23, 2018

(30) Foreign Application Priority Data

Oct. 22, 2015 (CN) .......................... 2015 1 0691295
Oct. 22, 2015 (CN) .......................... 2015 1 0691515

(51) Int. Cl.
| | | |
|---|---|---|
| C12N 15/82 | (2006.01) |
| A01N 47/44 | (2006.01) |
| C07K 14/37 | (2006.01) |
| A01N 37/46 | (2006.01) |
| A01H 3/04 | (2006.01) |
| A01N 63/10 | (2020.01) |
| C07K 14/415 | (2006.01) |

(52) U.S. Cl.
CPC .............. *A01N 47/44* (2013.01); *A01H 3/04* (2013.01); *A01N 37/46* (2013.01); *A01N 63/10* (2020.01); *C07K 14/37* (2013.01); *C07K 14/415* (2013.01); *C12N 15/825* (2013.01); *C12N 15/8242* (2013.01); *C12N 15/8243* (2013.01); *C12N 15/8245* (2013.01); *C12N 15/8249* (2013.01); *C12N 15/8261* (2013.01); *C12N 15/8266* (2013.01); *C12N 15/8267* (2013.01); *C12N 15/8273* (2013.01)

(58) Field of Classification Search
None
See application file for complete search history.

(56) References Cited

FOREIGN PATENT DOCUMENTS

| CN | 1609120 A | * | 4/2005 | ........... C07K 14/415 |
|---|---|---|---|---|
| CN | 1266163 C | * | 7/2006 | |
| CN | 102558320 A | | 7/2012 | |
| CN | 104558130 A | * | 4/2015 | ............... C12N 5/10 |
| CN | 104558130 A | | 4/2015 | |
| CN | 105198967 A | | 12/2015 | |
| CN | 105218649 A | | 1/2016 | |
| WO | 2015104698 A2 | | 7/2015 | |

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
McConnell et al. (Nature, 411:709-713, 200).*
Hanzawa et al. (PNAS, 102:7748-7753, 2005).*
Wishart et al. (JBC, 270:26782-26785, 1995).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Wang et al. (Appl. Environ. Microbiol. 70:4989-4995; 2004).*
Jian-Ying Wang, et al., "VdNEP, an Elicitor from Verticillium dahliae, InducesCotton Plant Wilting", Applied and Environmental Microbiology, Aug. 2004, p. 4989-4995, vol. 70, No. 8, American Society for Microbiology.
Bryan A. Bailey, "Purification of a Protein from Culture Filtrates of Fusarium oxysporum that Induces Ethylene and Necrosis in Leaves of Erythroxylum coca", Phytopathology, Oct. 1995, pp. 1250-1255, vol. 85, No. 10, Biochemistry and Cell Biology.
Guido Fellbrich, et al., "NPP1, a Phytophthora-associated trigger of plant defense in parsley and *Arabidopsis*", The Plant Journal, Aug. 22, 2002, (2002), 32, pp. 375-390, Blackwell Publishing Ltd.
Jingjing Yuan, "A Study on Factory Production and Field application of Plant Activator Protein", Sep. 1, 2009, Master Thesis, Chinese Academy of Agricultural Sciences.

(Continued)

*Primary Examiner* — Vinod Kumar
(74) *Attorney, Agent, or Firm* — Soroker Agmon Nordman Pte Ltd

(57) ABSTRACT

Provided are applications of protein VdAL in improving the output, product quality and drought resistance of a plant and in improving fruit coloring of the plant. The protein VdAL is selected from one of A1) to A3): A1), protein having an amino acid sequence that is 1; A2) protein that is derived from A), that has same functions and that is obtained by substituting and/or deleting and/or adding one or several amino acid residues for, from or to the sequence 1; and A3) fusion protein obtained by connecting labels to an N end and/or a C end of A1) or A2).

5 Claims, 10 Drawing Sheets
Specification includes a Sequence Listing.

(56) References Cited

OTHER PUBLICATIONS

Verticillium dahliae allergen Asp f2-like protein mRNA, complete cds, GenBank: AY524791.1, FASTA.
Verticillium dahliae necrosis and ethylene inducing peptide mRNA, complete cds, GenBank: AY524789.1, FASTA.

* cited by examiner

The Yield Per Mu (kg/mu)

APPLICATIONS OF PROTEIN VDAL IN IMPROVING OUTPUT, PRODUCT QUALITY AND DROUGHT RESISTANCE OF PLANT AND IN IMPROVING FRUIT COLORING OF PLANT

TECHNICAL FIELD

The present invention relates to the applications of protein VdAL in increasing the yield, product quality and drought resistance of plant and promoting coloration of plant fruit in the field of biotechnology.

TECHNICAL BACKGROUND

At present, sustainable high yield of cereals and economic crops planted at a large scale mainly depends on heavy use of chemical fertilizers, and heavy spray of chemical pesticides to prevent and control diseases and pests in China. When talking about agricultural pollution, a researcher at Institute of Agricultural Economics and Development, Chinese Academy of Agricultural Sciences pointed out that there are still quite serious problems in excessive use of fertilizers and pesticides, and heavy use of antibiotics and heavy metal additives in the breeding industry in China, and all of these will cause serious pollution to agricultural production (Hu Dinghuan, 2013).

According to the statistics of Liaoning Province alone, the annual use of fertilizers is over 30,000 tons at present, the strength of fertilizer application per unit area mu (equal to 666.7 $m^2$) is about 340 kg per hectare, the construction of national ecological area requires that the limit per hectare is 250 kg per hectare, widespread nonstandard fertilization that nitrogen fertilizer attracts more attention while phosphate and potash fertilizer are neglected is relatively outstanding, and the annual consumption of pesticides in Liaoning Province is over 14,000 tons and is increasing year by year. Residual pesticides, which enter the environment and agricultural products in the forms of atmospheric sedimentation and rain drop erosion, can easily cause environmental pollution events. In recent years, as the problem of rural environmental pollution has become more and more prominent, environmental complaint cases have increased. A few years ago, the provincial environmental complaint cases averaged 4,310 cases per year, of which nearly 2,795 were related to agricultural cases and accounted for about 65% of the complaint cases.

Excessive fertilization may cause increased antagonism of ions when crops absorb nutritive elements. If certain nutrient ions present in high-concentration can inhibit the activities of another one nutrient ion or more nutrient ions, the absorption of another nutrient ion in crops is affected. If excessive nitrogen fertilizer is applied to acid soil, it is difficult for crops to absorb calcium ions. If the calcium fertilizer is applied excessively, it may induce the lack of trace elements such as zinc, boron, iron, magnesium, manganese and the like in crops. Excessive potash fertilizer will also affect the absorption of calcium ions and magnesium ions in crops. Excessive fertilization can further easily cause crop poisoning. The increased concentration of a soil solution due to the application of a large amount of fertilizer causes the roots of crops to absorb water difficultly, the ground parts to wilt and plants to die. Moreover, excessive fertilization also affects the quality of agricultural products. The application of a lot of fertilizer during middle and later growth periods of crop decreases the sugar content of agricultural product organs and the storage ability of the agricultural product, so that the commodity value is affected and the economic benefits of crops are reduced.

SUMMARY OF THE INVENTION

The first technical problem to be solved by the present invention is how to promote the growth of plant and increase the yield of plant.

In order to solve the above technical problem, the present invention firstly provides an application of protein in increasing the yield of plant and/or regulating the growth of plant.

In the application of the protein provided in the present invention in increasing the yield of plant and/or regulating the growth of plant, the protein, named VdAL, is a protein of A1) or A2) or A3) as follows:

A1) a protein having an amino acid sequence shown in SEQ ID No. 1;

A2) a protein derived from A1) and obtained by substitution and/or deletion and/or addition of one or several amino acid residues of the amino acid sequence shown in SEQ ID No. 1, and having the same function with A1); and A3) a fusion protein labeled a tag at an N-terminal end or/and a C-terminal end of A1) or A2), wherein SEQ ID No. 1 consists of 297 amino acids.

In order to facilitate purification of the protein of A1), a tag shown in Table 1 can be labeled at the amino-terminal or the carboxyl-terminal of the protein shown in SEQ ID No. 1 or the amino acid of SEQ ID) No. 1 in the Sequence Listing.

TABLE 1

Tag sequences

| Tag | The number of Residues | Sequence |
| --- | --- | --- |
| Poly-Arg | 5-6 (Generally 5) | RRRRR |
| Poly-His | 2-10 (Generally 6) | HHHHHH |
| FLAG | 8 | DYKDDDDK |
| Strep-tag II | 8 | WSHPQFEK |
| c-myc | 10 | EQKLISEEDL |

The VdAL of A2) mentioned above can be artificially synthesized, or obtained by synthesis of the encoding gene thereof and then biological expression. The encoding gene of the VdAL of A2) mentioned above can be obtained by deletion of codon(s) of one or more amino acid residues from the DNA sequence shown in SEQ ID No. 2 in the Sequence Listing, and/or missense mutation of one or more base pairs therein, and/or ligation of the encoding sequence of a tag shown in table 1 at 5'-end and/or 3'-end thereof.

In the above application of the VdAL in increasing the yield of plant and/or regulating the growth of plant, said regulating the growth of plant may be plant growth promotion.

In order to solve the above technical problem, the present invention further provides an application of a biomaterial related to the VdAL in increasing the yield of plant and/or regulating the growth of plant.

In the application of the biomaterial related to the VdAL, provided in the present invention, in increasing the yield of plant and/or regulating the growth of plant, said biomaterial is any one of B1) to B20) as follows:

B1) a nucleic acid molecule encoding VdAL;

B2) an expression cassette comprising the nucleic acid molecule of B1);

B3) a recombinant vector comprising the nucleic acid molecule of B1);

B4) a recombinant vector comprising the expression cassette of B2);

B5) a recombinant microorganism comprising the nucleic acid molecule of B1);

B6) a recombinant microorganism comprising the expression cassette of B2);

B7) a recombinant microorganism comprising the recombinant vector of B3);

B8) a recombinant microorganism comprising the recombinant vector of B4);

B9) a genetically modified plant cell line comprising the nucleic acid molecule of B1);

B10) a genetically modified plant cell line comprising the expression cassette of B2);

B11) a genetically modified plant cell line comprising the recombinant vector of B3);

B12) a genetically modified plant cell line comprising the recombinant vector of B4);

B13) a genetically modified plant tissue comprising the nucleic acid molecule of B1);

B14) a genetically modified plant tissue comprising the expression cassette of B2);

B15) a genetically modified plant tissue comprising the recombinant vector of B3);

B16) a genetically modified plant tissue comprising the recombinant vector of B4);

B17) a genetically modified plant organ comprising the nucleic acid molecule of B1);

B18) a genetically modified plant organ comprising the expression cassette of B2);

B19) a genetically modified plant organ comprising the recombinant vector of B3); and B20) a genetically modified plant organ comprising the recombinant vector of B4).

In the above application of the biomaterial related to the VdAL in increasing the yield of plant and/or regulating the growth of plant, said nucleic acid molecule of B1) may be a gene of b1) or b2) or b3) as follows:

b1) a cDNA molecule or a DNA molecule having a nucleotide sequence shown in SEQ ID No. 2 in the Sequence Listing;

b2) a cDNA molecule or a genome DNA molecule having 75% or more identity with the nucleotide sequence defined by b1) and encoding the VdAL; and b3) a cDNA molecule or a genome DNA molecule hybridized, under stringent conditions, with the nucleotide sequence defined by b1) and encoding the VdAL.

Said nucleic acid molecule may be DNA, such as cDNA, genome DNA or recombinant DNA, and said nucleic acid molecule may also be RNA, such as mRNA or hnRNA, etc.

SEQ ID No. 2 consists of 894 nucleotides encoding the protein shown in SEQ ID No. 1.

The nucleotide sequence encoding the VdAL of the present invention can be readily mutated using a method known by those of ordinary skill in the art, such as a method of directed evolution or point mutation. Those artificially modified nucleotides having 75% or higher identity with the nucleotide sequence of the isolated VdAL of the present invention are all derived from the nucleotide sequence of the present invention and equivalent to the sequence of the present invention, as long as they encode the VdAL and have the same functions as the VdAL.

The term "identity" used herein refers to sequence similarity with a natural nucleotide sequence. The "identity" includes a nucleotide sequence having 75% or higher, 85% or higher, 90% or higher or 95% or higher identity with the nucleotide sequence encoding the protein consisted of the amino acid sequence shown as the VdAL of the present invention. The identity can be evaluated with naked eyes or computer software. When the computer software is used, the identity between two or more sequences can be expressed by percentage (%), which can be used to evaluate identity between the relevant sequences.

In the above application of the biomaterial related to the VdAL in increasing the yield of plant and/or regulating the growth of plant, said stringent condition refers to hybridization at 68° C. in 2×SSC buffer with 0.1% SDS, followed by washing the membrane twice for 5 min each time, and then hybridization at 68° C. in 0.5×SSC buffer with 0.1% SDS, followed by washing the membrane twice for 15 min each time; or alternatively hybridization at 65° C. in 0.1× SSPE (or 0.1×SSC) buffer with 0.1% SDS, followed by washing the membrane.

Said 75% or more identity may be 80%, 85%, 90% or 95% or higher identity.

In the above application of the biomaterial related to the VdAL in increasing the yield of plant and/or regulating the growth of plant, the expression cassette, comprising the nucleic acid molecule encoding the VdAL, of B2), i.e. VdAL gene expression cassette, refers to a DNA capable of expressing the VdAL in a host cell. Said DNA may comprise not only a promoter that initiates the transcription of the VdAL gene, but also a terminator that terminates the transcription of the VdAL gene. Further, the expression cassette may further comprise an enhancer sequence. The promoter that can be used in the present invention includes, but not limited to, a constitutive promoter, a tissue-, an organ- and a development-specific promoter, and an inducible promoter. The examples of the promoter include, but not limited to, a constitutive promoter 35S of cauliflower mosaic virus; a trauma-induced promoter from tomato, leucine aminopeptidase ("LAP", Chao et al. (1999) Plant Physiol 120: 979-992); a chemically inducible promoter from tobacco, pathogenesis-related 1 (PR1) (induced by salicylic acid and BTH (benzothiadiazole-7-carbothiolic acid S-methyl ester)); a tomato protease inhibitor II promoter (PIN2) or an LAP promoter which can be induced by methyl jasmonate, respectively, a heat shock promoter (U.S. Pat. No. 5,187,267); a tetracycline-inducible promoter (U.S. Pat. No. 5,057,422); a seed-specific promoter, such as a millet (*Setaria italica*) seed-specific promoter pF128 (CN101063139B, with a filing number of CN 200710099169.7), and a seed storage protein-specific promoter (e.g., phaseolin, napin, oleosin and soybean beta conglycin promoter (Beachy et al. (1985) EMBO J. 4: 3047-3053)). They can be used separately or in combination with other plant promoters. All references cited herein are incorporated herein by reference in their entireties. Suitable transcription terminator includes, but not limited to, a nopaline synthase terminator (NOS terminator) of *Agrobacterium*, a cauliflower mosaic virus (CaMV) 35S terminator, a tml terminator, a rbcS E9 terminator of pea and a terminator of nopaline or octopine synthase (see, e.g., Odell et al. (1985) Nature 313: 810; Rosenberg et al. (1987) Gene, 56: 125: Guerineau et al. (1991) Mol. Gen. Genet, 262: 141; Proudfoot (1991) Cell, 64: 671; Sanfacon et al. Genes Dev., 5: 141; Mogen et al. (1990) Plant Cell, 2: 1261; Munroe et al. (1990) Gene, 91: 151; Ballad et al. (1989) Nucleic Acids Res. 17: 7891; and Joshi et al. (1987) Nucleic Acid Res., 15: 9627).

A recombinant vector containing the expression cassette of the VdAL gene can be constructed via the existing expression vector. The plant expression vector comprises a binary *Agrobacterium tumefaciens* vector, and an expression vector that can be used for microprojectile bombardment in plant, such as, pAHC25, pBin438, pCAMBIA1302, pCAMBIA2301, pCAMBIA1301, pCAMBIA1300, pBI121, pCAMBIA1391-Xa or pCAMBIA1391-Xb (CAMBIA Company), etc. The plant expression vector may further comprise a 3'-untranslated region of an exogenous gene, i.e., a polyadenylation signal and any other DNA fragment involved in mRNA processing or gene expression. The polyadenylation signal can lead polyadenylation to be added to the 3'-end of an mRNA precursor. For example, the 3'-end transcribed untranslated region of gene in plasmid induced by *Agrobacterium* crown gall (Ti) (e.g., nopaline synthase gene Nos) or of plant gene (e.g., soybean storage protein gene) has a similar function. When the plant expression vector is constructed via the gene of the present invention, an enhancer including a translational enhancer or a transcriptional enhancer can also be used. Enhancer region, which can be ATG initiation codon, or initiation codon in the contiguous region, etc., must be identical to the reading frame of an encoding sequence, so as to ensure correct translation of the entire sequence. The translation control signal and the initiation codon, which have a wide variety of sources, may be either natural or synthetic. The translation initiation region may be derived from a transcription initiation region or a structural gene. In order to facilitate identification and screen of the genetically modified plant cell or plant, a plant expression vector can be constructed through, e.g., addition of a gene that can be expressed in plant and encodes an enzyme producing a color or synthesizes a luminescent compound (e. g., GUS gene, luciferase gene, etc), an antibiotic marker gene (e.g., an nptII gene that confers resistance kanamycin and relevant antibiotics resistance, a bar gene that confers resistance herbicide phosphinothricin, an hph gene that confers resistance antibiotic hygromycin, a dhfr gene that confers resistance methotrexate, and an EPSPS gene that confers resistance glyphosate), an anti-chemical reagent marker gene (such as a herbicide-resistant gene), or a mannose-6-phosphate isomerase gene that provides the ability of mannose metabolism, etc. In consideration of safety of genetically modified plant, any selective marker gene may not be contained, while plants are directly screened and transformed under adverse circumstances.

In the above application of the biomaterial related to the VdAL in increasing the yield of plant and/or regulating the growth of plant, the vector may be plasmid, cosmid, phage or virus vector. The plasmid may be vector pET42a (+).

In the above application of the biomaterial related to the VdAL in increasing the yield of plant and/or regulating the growth of plant, the microorganism may be yeast, bacteria, algae or fungi, such as *Escherichia coli*. *Escherichia coli* may be *Escherichia coli* JM109.

In the above application of the biomaterial related to the VdAL in increasing the yield of plant and/or regulating the growth of plant, the genetically modified plant cell line, the genetically modified plant tissue and the genetically modified plant organ may or may not include a propagating material, respectively.

In the above application of the biomaterial related to the VdAL in increasing the yield of plant and/or regulating the growth of plant, the genetically modified plant organ may also be seeds of a genetically modified plant. The genetically modified plant may include seeds, callus, whole plant and cells.

In one embodiment of the present invention, a recombinant microorganism is obtained by the transformation of a recombinant vector comprising an expression cassette comprising the encoding gene of the VdAL into *Escherichia coli* JM109. The recombinant vector is obtained by replacing a sequence between NdeI and KpnI recognition sites of a vector pET42a (+) with the DNA molecule, namely VdAL gene, represented by nucleotides $1^{st}$ to $894^{th}$ of SEQ ID No. 2 in the Sequence Listing. The recombinant vector expresses the VdAL shown in SEQ ID No. 1. The recombinant microorganism expresses the VdAL shown in SEQ ID No. 1.

In the above application of the biomaterial related to the VdAL in increasing the yield of plant and/or regulating the growth of plant, said regulating the growth of plant may be plant growth promotion.

In order to solve the above technical problem, the present invention further provides a method for increasing the yield of plant and/or promoting plant growth.

The method of increasing the yield of plant and/or promoting the growth of plant according to the present invention comprises a step of applying the VdAL, the biomaterial or the biological agent to a target plant, so as to increase the yield of the target plant and/or promote the growth of the target plant. The active ingredient of the biological agent is the VdAL or the biomaterial.

In the above method, the biological agent can be prepared by method 1). Said method 1) is that the recombinant microorganism is cultivated to express the encoding gene of the VdAL to obtain the biological agent.

In the above method, said method 1) may specifically comprise 11) and 12) as follows:

11) cultivating the recombinant microorganism to express the encoding gene to obtain a culture of the recombinant microorganism expressing the protein; and 12) disrupting thalli of the microorganism culture to obtain the biological agent.

In the above method, said method 1) may further include a step of drying the biological agent.

In the above method, the encoding gene may be the nucleic acid molecule of B1).

In one embodiment of the present invention, the recombinant microorganism is obtained by the transformation of the recombinant vector comprising an expression cassette comprising the encoding gene of the VdAL into *Escherichia coli* JM109. The recombinant vector is obtained by replacing a sequence between NdeI and KpnI recognition sites of a vector pET42a (+) with the DNA molecule, namely VdAL gene, represented by nucleotides $1^{st}$ to $894^{th}$ of SEQ ID No. 2. The recombinant vector expresses the VdAL shown in SEQ ID No. 1. The recombinant microorganism expresses the VdAL shown in SEQ ID No. 1.

In the above method, the step of applying the VdAL, the biomaterial or the biological agent to a target plant may specifically be a step of applying the VdAL, the biomaterial or the biological agent to leaves of the target plant, e.g., spraying the VdAL, the biomaterial or the biological agent to the target plant; or treating seeds of the target plant with the VdAL, the biomaterial or the biological agent, e.g., soaking the seeds of the target plant into a liquid agent of the VdAL, the biomaterial or the biological agent. The liquid agent of the VdAL, the biomaterial or the biological agent may be the liquid obtained by directly dissolving or suspending the VdAL, the biomaterial or the biological agent into clear water. The quantity of the VdAL, the biomaterial or the biological agent applied to the target plant may be determined according to species and/or growth phase of the target plant.

In order to solve the above technical problem, the present invention further provides an application of the biological agent in increasing the yield of plant and/or regulating the growth of plant.

In order to solve the above technical problem, the present invention further provides the biological agent. In the present invention, the name of the biological agent is the agent of VdAL.

In the above description, the plant is a plant of Dicotyledoneae or a plant of Monocotyledonae. Said plant of Dicotyledoneae may be a plant of Malvaceae, Cucurbitaceae, Solanaceae, Cruciferae, Rosaceae, Vitaceae, Prunoideae, Chenopodiaceae or Leguminosac. The plant of Malvaceae may be cotton. The plant of Cucurbitaceae may be watermelon, cucumber or melon. The plant of Solanaccae may be tomato, cherry tomato or eggplant. The plant of Cruciferae may be green-stem cabbage or radish, e.g., can-like radish. The plant of Rosaceae may be strawberry. The plant of Leguminosac may be soybean. The plant of Vitaceac may be grape. The plant of Prunoideae may be cherry. The plant of Chenopodiaceae may be spinach. The plant of Monocotyledonae may be the plant of Poaceae, such as rice or wheat.

In the above description, the yield may be economic yield, i.e., the yield mass of product needed by the purpose of cultivation, e.g., seeds of cereals; unginned cotton or ginned cotton of cotton; plant of green-stem cabbage or spinach; fruits of watermelon, tomato, cucumber, cherry tomato, strawberry, melon, sweet pepper, cherry and grape; and tuberous root of radish. The yield can be reflected in weight.

In production, said promoting plant growth may be finally reflected as the increased yield of the crop, e.g., the increased yield of cotton, watermelon, wheat, tomato, green-stem cabbage, cucumber, cherry tomato, strawberry, melon, rice, grape, cherry, radish, spinach, sweet pepper or soybean.

In the above description, promoting plant growth may be vegetative growth promotion and/or reproductive growth promotion of plant, e.g., promoting the growth of plant fruit. The vegetative growth can specifically be reflected as promoting seed germination, promoting plant growth, promoting fruit growth, improving the number of fruit setting and/or delaying plant aging. In the embodiments of the present invention, promoting vegetative growth of plant is specifically reflected as the following several aspects: improving the germination rate, the number of boll setting of individual plant, the total number of the boll per mu and the weight of single boll of cotton; improving the number of individual plant of watermelon; improving the germination rate of wheat and promoting plant growth of wheat; improving the fruit number of individual plant of tomato; promoting growth of plant of green-stem cabbage, spinach or radish; improving the number of fruit setting of cucumber, promoting fruit expansion of cucumber, promoting growth of cucumber plant, and delaying aging of cucumber plant; improving the number of fruit setting of cherry tomato, cherry and grape; promoting growth of strawberry plant; promoting growth of melon plant; promoting growth of sweet pepper plant; and promoting seedling emergence of soybean and growth of plant thereof. Said promoting reproductive growth of plant is specifically reflected as improving the number of fruit setting of cotton, watermelon, tomato, cucumber and cherry tomato.

In the above text, the effects of the VdAL or the biological agent on different plants may be different due to different concentrations thereof. When the VdAL or the biological agent is applied, the concentration of the VdAL or the biological agent can be adjusted according to a crop or a variety thereof and the purpose of applying the VdAL or the biological agent (e.g., promoting seed germination or improving the biological yield, etc.).

In an embodiment of the present invention, the liquid obtained by diluting the biological agent 7,500 times can promote germination of cotton. The liquid obtained by diluting the biological agent 3,000-5,000 times can improve the cotton yield before first frost, total yield, plant number per mu, the number of boll setting of individual plant, total boll number per mu, ginning outturn and the yield per mu. The liquid obtained by diluting the biological agent 2,000 times can promote watermelon fruit and improve the yield of watermelon. The liquid obtained by diluting the biological agent 5,000-10,000 times can promote germination of wheat seeds; and the liquid obtained by diluting the biological agent 5,000-20,000 times can improve the yield of wheat. The liquid obtained by diluting the biological agent 1.000 times can promote tomato fruit and improve the yield of tomato. The liquid obtained by diluting the biological agent 2,000-4,000 times can improve the yield of green-stem cabbage. The liquid obtained by diluting the biological agent 300-2,000 times can improve the rate of fruit setting of cucumber, promote expansion of cucumber, improve the yield of cucumber, promote apical growth of cucumber plant and delay aging of cucumber plant. The liquid obtained by diluting the biological agent 2,000 times can improve the rate of fruit setting of cherry tomato. The liquid obtained by diluting the biological agent 2,000 times can promote the growth of plant of strawberry and melon. The liquid obtained by diluting the biological agent 1,000 times can promote the growth of plant of sweet pepper. The liquid obtained by diluting the biological agent 3,000-5,000 times can promote seedling emergence and growth of soybean. The liquid obtained by diluting the biological agent 10,000-20,000 times can improve the yield of rice. The liquid obtained by diluting the biological agent 3,000 times can promote the maturity of grape. The liquid obtained by diluting the biological agent 5,000 times can promote the maturity of cherry and the growth of radish. The liquid obtained by diluting the biological agent 6,000 times can promote the growth of spinach.

The second technical problem to be solved by the present invention is how to improve the quality of plant product. The plant product is a desired product of plant cultivated and produced by human beings. The evaluation criteria of the quality can vary due to different application of the product. The quality of a product serving as food can be reflected as nutritional quality of the product and eating quality thereof. The quality of a product serving as a clothing material can be reflected as fiber quality of the product. Two indicators are usually adopted to evaluate the product quality. One is the content of biochemical components and harmful substances, such as nutrient content and trace element content; and the other one is a physical indicator, such as shape, size, flavor, aroma, color, thickness of seed coat, uniformity, fiber length, fiber strength and the like of the product, e.g., ginning outturn of cotton.

In order to solve the above technical problem, the present invention firstly provides an application of protein in improving the quality of plant product.

In the application of the protein in improving the quality of plant product, the protein is named VdAL, and is A1) or A2) or A3) as follows:

A1) a protein having an amino acid sequence shown in SEQ ID No. 1;

A2) a protein derived from A1) and obtained by substitution and/or deletion and/or addition of one or several amino acid residues of the amino acid sequence shown in SEQ ID No. 1 and having the same function as A1); and A3) a fusion protein labeled a tag at an N-terminal end or/and a C-terminal end of A1) or A2), wherein SEQ ID No. 1 consists of 297 amino acids.

In order to facilitate purification of the protein of A1), a tag shown in Table 1 can be labeled at the amino-terminal or carboxyl-terminal of the protein shown in SEQ ID No. 1 in a Sequence Listing.

The VdAL of A2) mentioned above can be artificially synthesized, or obtained by synthesis of the encoding gene thereof and then biological expression. The encoding gene of the VdAL of A2) mentioned above can be obtained by deletion of codon(s) of one or more amino acid residues from the DNA sequence shown in SEQ ID No. 2 in the Sequence Listing, and/or missense mutation of one or more base pairs therein, and/or ligation of the encoding sequence of a tag shown in table 1 at 5'-end and/or 3'-end thereof.

In the above application of the VdAL in improving the quality of plant product, said improving the quality of plant product may be nutrient content improvement of plant product and/or the content improvement of trace elements of plant product and/or palatability improvement of plant product. The nutrient ingredient of plant product may specifically be vitamin C, soluble sugar and/or protein. The trace elements may specifically be Cu, Fe, K, Mn and/or Zn. The palatability may be reflected as the decreased dry matter content and/or content of coarse fibers, or the brittleness of the edible part of plant.

In the above application of the VdAL in improving the quality of plant product, the quality of plant product can be improved by promoting the maturity of plant product. In one embodiment of the present invention, the VdAL is applied to promote the maturity of cotton product and to increase the yield of cotton before first frost, so as to improve the quality of cotton.

In the above application of the VdAL in improving the quality of plant product, the plant may be a plant of Dicotyledoneae or a plant of Monocotyledonae.

In the above application of the VdAL in improving the quality of plant product, the plant of Dicotyledoneae may be a), b), c), d), e), f), g) or h) below: a) a plant of Cucurbitaceae; b) watermelon; c) a plant of Malvaceae; d) cotton; e) a plant of Vitaceae; f) grape; g) a plant of Cruciferae; and h) radish.

In order to solve the above technical problem, the present invention further provides an application of a biomaterial related to the VdAL in improving the quality of plant product.

In the application of the biomaterial related to the VdAL in improving the quality of plant product, the biomaterial is one of B1) to 120) as follows:

B1) a nucleic acid molecule encoding VdAL;

B2) an expression cassette containing the nucleic acid molecule of B1);

B3) a recombinant vector comprising the nucleic acid molecule of B1);

B4) a recombinant vector comprising the expression cassette of B2);

B5) a recombinant microorganism comprising the nucleic acid molecule of B1);

B6) a recombinant microorganism comprising the expression cassette of B2);

B7) a recombinant microorganism comprising the recombinant vector of B3);

B8) a recombinant microorganism comprising the recombinant vector of B4);

B9) a transgenic plant cell line comprising the nucleic acid molecule of B1);

B10) a genetically modified plant cell line comprising the expression cassette of B2);

B11) a genetically modified cell line comprising the recombinant vector of B3);

B12) a genetically modified plant cell line comprising the recombinant vector of B4);

B13) a genetically modified plant tissue comprising the nucleic acid molecule of B1);

B14) a genetically modified plant tissue comprising the expression cassette of B2);

B15) a genetically modified plant tissue containing the recombinant vector of B3);

B16) a genetically modified plant tissue comprising the recombinant vector of B4);

B17) a genetically modified plant organ comprising the nucleic acid molecule of B1);

B18) a genetically modified plant organ comprising the expression cassette of B2);

B19) a genetically modified plant organ comprising the recombinant vector of B3); and B20) a genetically modified plant organ comprising the recombinant vector of B4).

In the above application of the biomaterial related to the VdAL in improving the quality of plant product, the nucleic acid molecule of B1) may be a gene of b1) or b2) or b3) as follows:

b1) a cDNA molecule or a DNA molecule having a nucleotide sequence shown in SEQ ID No. 2 in the Sequence Listing;

b2) a cDNA molecule or a genome DNA molecule having 75% or more identity with the nucleotide sequence defined by b1) and encoding the VdAL;

b3) a cDNA molecule or a genome DNA molecule hybridized, under stringent conditions, with the nucleotide sequence defined by b1) and encoding the VdAL.

wherein, said nucleic acid molecule may be DNA, such as cDNA, genome DNA or recombinant DNA, and said nucleic acid molecule may also be RNA, such as mRNA or hnRNA, etc.

and SEQ ID No. 2 consists of 894 nucleotides encoding the protein shown in SEQ ID No. 1.

The nucleotide sequence encoding the VdAL of the present invention can be readily mutated using a method known by those of ordinary skill in the art, such as a method of directed evolution and point mutation. Those artificially modified nucleotides having 75% or higher identity with the nucleotide sequence of the isolated VdAL of the present invention are all derived from the nucleotide sequence of the present invention and equivalent to the sequence of the present invention, as long as they encode the VdAL and have the same functions as the VdAL.

The term "identity" used herein refers to sequence similarity with a natural nucleotide sequence. The "identity" includes a nucleotide sequence having 75% or higher, 85% or higher, 90% or higher or 95% or higher identity with the nucleotide sequence encoding the protein consisted of the amino acid sequence shown as the VdAL of the present invention. The identity can be evaluated with naked eyes or computer software. When the computer software is used, the identity between two or more sequences can be expressed by percentage (%), which can be used to evaluate identity between the relevant sequences.

In the above application of the biomaterial related to the VdAL in improving the quality of plant product, the stringent condition refers to hybridization at 68° C. in 2×SSC buffer with 0.1% SDS, followed by washing the membrane twice for 5 min each time, and then hybridization at 68° C. in 0.5×SSC buffer with 0.1% SDS, followed by washing the membrane twice for 15 min each time; or alternatively hybridization at 65° C. in 0.1×SSPE (or 0.1×SSC) buffer with 0.1% SDS, followed by washing the membrane.

Said 75% or more identity may be 80%, 85%, 90% or 95% or higher identity.

In the above application of the biomaterial related to the VdAL in improving the quality of plant product, the expression cassette, comprising the nucleic acid molecule encoding the VdAL, of B2), i.e. the VdAL gene expression cassette, refers to a DNA capable of expressing the VdAL in a host cell. Said DNA may comprise not only a promoter that initiates the transcription of the VdAL gene, but also a terminator that terminates the transcription of the VdAL gene. Further, the expression cassette may further comprise an enhancer sequence. The promoter that can be used in the present invention includes, but not limited to, a constitutive promoter, a tissue-, an organ- and a development-specific promoter; and an inducible promoter. The examples of the promoter include, but not limited to, a constitutive promoter 35S of cauliflower mosaic virus; a trauma-induced promoter from tomato, leucine aminopeptidase ("LAP", Chao et al. (1999) Plant Physiol 120: 979-992); a chemically inducible promoter from tobacco, pathogenesis-related 1 (PR1) (induced by salicylic acid and BTH (benzothiadiazole-7-carbothiolic acid S-methyl ester)); a tomato protease inhibitor II promoter (PIN2) or an LAP promoter (both can be induced by methyl jasmonate); a heat shock promoter (U.S. Pat. No. 5,187,267); a tetracycline-inducible promoter (U.S. Pat. No. 5,057,422); a seed-specific promoter, such as a millet (*Setaria italica*) seed-specific promoter pF128 (CN101063139B, with a filing number of CN 200710099169.7), and a seed storage protein-specific promoter (e.g., phaseolin, napin, oleosin and soybean beta conglycin promoter (Beachy et al. (1985) EMBO J. 4: 3047-3053)). They can be used separately or in combination with other plant promoters. All references cited herein are incorporated herein by reference in their entireties. Suitable transcription terminator includes, but not limited to, a nopaline synthase terminator (NOS terminator) of *Agrobacterium*, a cauliflower mosaic virus (CaMV) 35S terminator, a tml terminator, a rbcS E9 terminator of pea and a terminator of nopaline or octopine synthase (see, e.g., Odell et al. (1985) Nature 313: 810; Rosenberg et al. (1987) Gene, 56: 125; Guerineau et al. (1991) Mol. Gen. Genet, 262: 141; Proudfoot (1991) Cell, 64: 671; Sanfacon et al. Genes Dev., 5: 141; Mogen et al. (1990) Plant Cell, 2: 1261; Munroe et al. (1990) Gene, 91: 151; Ballad et al. (1989) Nucleic Acids Res. 17: 7891; and Joshi et al. (1987) Nucleic Acid Res., 15: 9627).

A recombinant vector containing the expression cassette of the VdAL gene can be constructed via the existing expression vector. The plant expression vector comprises a binary *Agrobacterium tumefaciens* vector, and an expression vector that can be used for microprojectile bombardment in plant, and the like, e.g., pAHC25, pBin438, pCAMBIA1302, pCAMBIA2301, pCAMBIA1301, pCAMBIA1300, pBI121, pCAMBIA1391-Xa or pCAMBIA1391-Xb (CAMBIA Company), etc. The plant expression vector may further comprise a 3'-untranslated region of an exogenous gene, i.e., a polyadenylation signal and any other DNA fragment involved in mRNA processing or gene expression. The polyadenylation signal can lead polyadenylation to be added to the 3'-end of an mRNA precursor, e.g., the 3'-end transcribed untranslated region of gene in plasmid induced by an *Agrobacterium* crown gall (Ti), e.g., nopaline synthase gene Nos, or of plant gene, e.g., soybean storage protein gene, has a similar function. When the plant expression vector is constructed via the gene of the present invention, an enhancer including a translational enhancer or a transcriptional enhancer can also be used. Enhancer region, which may be ATG initiation codon, or initiation codon in the contiguous region, etc., must be identical to the reading frame of an encoding sequence, so as to ensure correct translation of the entire sequence. The translation control signal and the initiation codon, which have a wide variety of sources, may be either natural or synthetic. The translation initiation region may be derived from a transcription initiation region or a structural gene. In order to facilitate identification and screen of the genetically modified plant cell or plant, a plant expression vector can be constructed through, e.g., addition of a gene that can be expressed in plant and encodes an enzyme producing a color or synthesizes a luminescent compound, i.e. GUS gene, luciferase gene, etc; an antibiotic marker gene, e.g., an nptII gene that confers resistance kanamycin and relevant antibiotics resistance, a bar gene that confers resistance herbicide phosphinothricin, an hph gene that confers resistance antibiotic hygromycin, a dhfr gene that confers resistance methotrexate, an EPSPS gene that confers resistance glyphosate; an anti-chemical reagent marker gene, such as a herbicide-resistant gene; or a mannose-6-phosphate isomerase gene that provides the ability of mannose metabolism, etc. In consideration of safety of genetically modified plant, any selective marker gene may not be added, while plants are directly screened and transformed under adverse circumstances.

In the above application of the biomaterial related to the VdAL in improving the quality of plant product, the vector may be a plasmid, cosmid, phage or virus vector. The plasmid may be vector pET42a (+).

In the above application of the biomaterial related to the VdAL in improving the quality of plant product, the microorganism may be yeast, bacteria, algae or fungi such as *Escherichia coli*. *Escherichia coli* may be *Escherichia coli* JM109.

In the above application of the biomaterial related to the VdAL in improving the quality of plant product, the genetically modified plant cell line, the genetically modified plant tissue and the genetically modified plant organ may or may not include a propagating material, respectively.

In the above application of the biomaterial related to the VdAL in improving the quality of plant product, the genetically modified plant organ may also be seeds of a genetically modified plant. The genetically modified plant may include seeds, callus, whole plant and cells.

In one embodiment of the present invention, a recombinant microorganism is obtained by the transformation of the recombinant vector comprising an expression cassette comprising the encoding gene of the VdAL into *Escherichia coli* JM109. The recombinant vector is obtained by replacing a sequence between NdeI and KpnI recognition sites of a vector pET42a (+) with the DNA molecule, namely VdAL gene, represented by nucleotides $1^{st}$ to $894^{th}$ of SEQ ID No. 2 in the Sequence Listing. The recombinant vector expresses the VdAL shown in SEQ ID No. 1. The recombinant microorganism expresses the VdAL shown in SEQ ID No. 1.

In the above application of the biomaterial related to the VdAL in improving the quality of plant product, said improving the quality of plant product may be improvement of nutrient content of plant product and/or improvement of content of trace elements of plant product and/or improvement of palatability of plant product. The nutrient ingredient of plant product may specifically be vitamin C, soluble sugar and/or protein. The trace elements may specifically be Cu, Fe, K, Mn and/or Zn. The palatability may be reflected as the decreased dry matter content and/or the content of coarse fibers.

In the above application of the biomaterial related to the VdAL in improving the quality of plant product, the quality of plant product can be improved by promoting maturity of plant product. In one embodiment of the present invention, the VdAL is applied to promote the maturity of the cotton product and to increase the yield of cotton before first frost, so as to improve the quality of cotton.

In the above application of the biomaterial related to the VdAL in improving the quality of plant product, the plant may be a plant of Dicotyledoneae or a plant of Monocotyledonae.

In the above application of the biomaterial related to the VdAL in improving the quality of plant product, the plant of Dicotyledoneae may be a), b), c), d), e), f), g) or h) as follows: a) a plant of Cucurbitaceae; b) watermelon; c) a plant of Malvaceae; d) cotton; e) a plant of Vitaceac; f) grape; g) a plant of Cruciferae; and h) radish.

In order to solve the above technical problem, the present invention further provides a method for improving the quality of plant product.

The method for improving the quality of plant product includes a step of applying the VdAL, the biomaterial or a biological agent to a target plant, so as to increase the quality of the target plant product. The active ingredient of the biological agent is the VdAL or the biomaterial.

In the above method for improving the quality of plant product, the biological agent can be prepared by method 1). Said method 1) is that the recombinant microorganism is cultivated to express the encoding gene of the VdAL to obtain the biological agent.

In the above method for improving the quality of plant product, said method 1) may specifically comprise 11) and 12) as follows:

11) cultivating the recombinant microorganism to express the encoding gene to obtain culture of recombinant microorganism expressing the protein; and 12) disrupting thalli of the microorganism culture to obtain a biological agent.

In the above method for improving the quality of plant product, said method 1) may further include a step of drying the biological agent.

In the above method for improving the quality of plant product, the encoding gene may be the nucleic acid molecule of B1).

In one embodiment of the present invention, the recombinant microorganism is obtained by the transformation of the recombinant vector comprising an expression cassette comprising the encoding gene of the VdAL into *Escherichia coli* JM109. The recombinant vector is obtained by replacing a sequence between NdeI and KpnI recognition sites of a vector pET42a (+) with the DNA molecule, namely VdAL gene, represented by nucleotides $1^{st}$ to $894^{th}$ nucleotides of SEQ ID No. 2. The recombinant vector expresses the VdAL shown in SEQ ID No. 1. The recombinant microorganism expresses the VdAL shown in SEQ ID No. 1.

In the above method for improving the quality of plant product, the step of applying the VdAL, the biomaterial or a biological agent to a target plant may specifically be a step of applying the VdAL, the biomaterial or the biological agent to leaves of the target plant, e.g., spraying the VdAL, the biomaterial or the biological agent to the target plant; or treating seeds of the target plant with the VdAL, the biomaterial or the biological agent, e.g., soaking the seeds of the target plant into a liquid agent of the VdAL, the biomaterial or the biological agent. The liquid agent of the VdAL, the biomaterial or the biological agent may be the liquid obtained by directly dissolving or suspending the VdAL, the biomaterial or the biological agent into clear water. The quantity of the VdAL, the biomaterial or the biological agent applied to the target plant may be determined according to species and/or growth phase of the target plant.

In the above method for improving the quality of plant product, said improving the quality of plant product may be improvement of the nutrient content of plant product and/or improvement of the content of trace elements of plant product and/or improvement of the palatability of plant product. The nutrient ingredient of plant product may specifically be vitamin C, soluble sugar and/or protein. The trace elements may specifically be Cu, Fe, K, Mn and/or Zn. The palatability may be reflected as the decreased dry matter content and/or the content of coarse fibers.

In the above method for improving the quality of plant product, the quality of plant product can be improved by promoting the maturity of plant product. In one embodiment of the present invention, the VdAL is applied to promote the maturity of cotton product and to increase the yield of cotton before first frost, so as to improve the quality of cotton.

In the above method for improving the quality of plant product, the plant may be a plant of Dicotyledoneae or a plant of Monocotyledonae.

In the above method for improving the quality of plant product, the plant of Dicotyledoneae may be a), b), c), d), e), f), g) or h) below: a) a plant of Cucurbitaceac; b) watermelon; c) a plant of Malvaceae; d) cotton; e) a plant of Vitaceae; f) grape; g) a plant of Cruciferae; and h) radish.

In order to solve the above technical problem, the present invention further provides an application of the biological agent in improving the quality of plant product.

In the above application of the biological agent in improving the quality of plant product, said improving the quality of plant product may be improvement of the nutrient content of plant product and/or improvement of the content of trace elements of plant product and/or improvement of the palatability of plant product. The nutrient ingredient of plant product may specifically be vitamin C, soluble sugar and/or protein. The trace elements may specifically be Cu, Fe, K, Mn and/or Zn. The palatability may be reflected as the decreased dry matter content and/or the content of coarse fibers, or brittleness of the edible part of plant.

In the above application of the biological agent in improving the quality of plant product, the quality of plant product can be improved by promoting the maturity of plant product. In one embodiment of the present invention, the VdAL is applied to promote the maturity of a cotton product and to increase the yield of cotton before first frost, so as to improve the quality of cotton.

In the above application of the biological agent in improving the quality of plant product, the plant may be a plant of Dicotyledoneae or a plant of Monocotyledonae.

In the above application of the biological agent in improving the quality of plant product, the plant of Dicotyledoneae may be a), b), c), d), e), f), g) or h) as follows: a) a plant of Cucurbitaceae; b) watermelon; c) a plant of Malvaceae; d) cotton; e) plant of Vitaceae; f) grape; g) a plant of Cruciferae; and h) radish.

In the above description, different concentrations of the VdAL or the biological agent leads to different results in the effects of the VdAL or the biological agent on different plants. When the VdAL or the biological agent is applied, the concentration of the VdAL or the biological agent can be adjusted according to a crop or a variety thereof and the purpose of applying the VdAL or the biological agent (e.g., improving the content of nutrients of the target plant product).

In an embodiment of the present invention, the liquid obtained by diluting the biological agent 2000 times can improve the content of nutrients and trace elements in watermelon. The liquid obtained by diluting the biological agent 3000-5000 times can improve the ginning outturn of cotton. The liquid obtained by diluting the biological agent 3000 times can improve the content of vitamin C in grape. The liquid obtained by diluting the biological agent 5000 times can improve brittleness and sweetness of can-like radish.

In the above description, the radish may be can-like radish.

The third technical problem to be solved by the present invention is how to improve drought resistance of plant or promote coloration of plant fruit.

In order to solve the above technical problem, the present invention firstly provides an application of protein in regulating drought resistance of plant or regulating coloration of plant fruit.

In the application of protein in regulating drought resistance of plant or regulating coloration of plant fruit, the protein is named VdAL, and is A1) or A2) or A3) as follows:

A1) a protein having the amino acid sequence shown in SEQ ID No. 1;

A2) a protein derived from A1) and obtained by substitution and/or deletion and/or addition of one or several amino acid residues of the amino acid sequence shown in SEQ ID No. 1, and having the same function with A1); and A3) a fusion protein labeled a tag at an N-terminal end or/and a C-terminal end of A1) or A2), wherein SEQ ID No. 1 consists of 297 amino acids.

In order to facilitate purification of the protein of A1), a tag shown in table 1 can be labeled at the amino-terminal or carboxyl-terminal of the protein shown in SEQ ID No. 1 in a Sequence Listing.

The VdAL of A2) mentioned above can be artificially synthesized, or obtained by synthesis of the encoding gene thereof and then biological expression. The encoding gene of the VdAL of A2) mentioned above can be obtained by deletion of codon(s) of one or more amino acid residues from the DNA sequence shown in SEQ ID No. 2 in the Sequence Listing, and/or missense mutation of one or more base pairs therein, and/or ligation of the enoding sequence of a tag shown in table 1 at 5'-end and/or 3'-end thereof.

In the above application of the VdAL in regulating the drought resistance of plant or regulating coloration of plant fruit, the plant may be a plant of Dicotyledoneae or a plant of Monocotyledonae.

In order to solve the above technical problem, the present invention further provides an application of a biomaterial related to the VdAL in regulating the drought resistance of plant or regulating coloration of plant fruit.

In the application of the biomaterial related to the VdAL in regulating the drought resistance of plant or regulating the coloration of plant fruit, the biomaterial is any one of B1) to B20) as follows:

B1) a nucleic acid molecule encoding VdAL;

B2) an expression cassette comprising the nucleic acid molecule of B1);

B3) a recombinant vector comprising the nucleic acid molecule of B1);

B4) a recombinant vector comprising the expression cassette of B2);

B5) a recombinant microorganism comprising the nucleic acid molecule of B1);

B6) a recombinant microorganism comprising the expression cassette of B2);

B7) a recombinant microorganism comprising the recombinant vector of B3);

B8) a recombinant microorganism comprising the recombinant vector of B4);

B9) a genetically modified plant cell line comprising the nucleic acid molecule of B1);

B10) a genetically modified plant cell line comprising the expression cassette of B2);

B11) a genetically modified plant cell line comprising the recombinant vector of B3);

B12) a genetically modified plant cell line comprising the recombinant vector of B4);

B13) a genetically modified plant tissue comprising the nucleic acid molecule of B1);

B14) a genetically modified plant tissue comprising the expression cassette of B2);

B15) a genetically modified plant tissue comprising the recombinant vector of B3);

B16) a genetically modified plant tissue comprising the recombinant vector of B4);

B17) a genetically modified plant organ comprising the nucleic acid molecule of B1);

B18) a genetically modified plant organ comprising the expression cassette of B2);

B19) a genetically modified plant organ comprising the recombinant vector of B3); and B20) a genetically modified plant organ comprising the recombinant vector of B4).

In the above application of the biomaterial related to the VdAL in regulating the drought resistance of plant or regulating the coloration of plant fruit, the nucleic acid molecule of B1) may be a gene of b1) or b2) or b3) as follows:

b1) a cDNA molecule or a DNA molecule having a nucleotide sequence shown in SEQ ID No. 2 in the Sequence Listing;

b2) a cDNA molecule or a genome DNA molecule having 75% or more identity with the nucleotide sequence defined by b1) and encoding the VdAL; and b3) a cDNA molecule or a genome DNA molecule hybridized, under stringent conditions, with the nucleotide sequence defined by b1) and encoding the VdAL.

Said nucleic acid molecule may be DNA, such as cDNA, genome DNA or recombinant DNA, said nucleic acid molecule may also be RNA, such as mRNA or hnRNA, etc.

SEQ ID No. 2 consists of 894 nucleotides encoding the protein shown in SEQ ID No. 1.

The nucleotide sequence encoding the VdAL of the present invention can be readily mutated using a method known by those of ordinary skill in the art, such as a method of directed evolution or point mutation. Those artificially modified nucleotides having 75% or higher identity with the nucleotide sequence of the isolated VdAL of the present invention are all derived from the nucleotide sequence of the present invention and equivalent to the sequence of the present invention, as long as they encode the VdAL and have the same functions as the VdAL.

The term "identity" used herein refers to sequence similarity with a natural nucleotide sequence. The "identity"

includes a nucleotide sequence having 75% or higher, 85% or higher, 90% or higher or 95% or higher identity with the nucleotide sequence encoding the protein consisted of the amino acid sequence shown as the VdAL of the present invention. The identity can be evaluated with naked eyes or computer software. When the computer software is used, the identity between two or more sequences can be expressed by percentage (%), which can be used to evaluate the identity between the relevant sequences.

In the above applications of the biomaterial related to the VdAL in regulating the drought resistance of a plant or regulating coloration of a plant fruit, said stringent condition refers to hybridization at 68° C. in 2×SSC buffer with 0.1% SDS, followed by washing the membrane twice for 5 min each time, and then hybridization at 68° C. in 0.5×SSC buffer with 0.1% SDS, followed by washing the membrane twice for 15 min each time; or alternatively hybridization at 65° C. in 0.1×SSPE (or 0.1×SSC) buffer with 0.1% SDS, followed by washing the membrane.

Said 75% or more identity may be 80%, 85%, 90% or 95% or higher identity.

In the above application of the biomaterial related to the VdAL in regulating the drought resistance of plant or regulating the coloration of plant fruit, the expression cassette, comprising the nucleic acid molecule encoding the VdAL, of B2), i.e. the VdAL gene expression cassette, refers to a DNA capable of expressing the VdAL in a host cell. Said DNA may comprise not only a promoter that initiates the transcription of the VdAL gene, but also a terminator that terminates the transcription of the VdAL gene. Further, the expression cassette may further comprise an enhancer sequence. The promoter that can be used in the present invention includes, but not limited to, a constitutive promoter; a tissue-, an organ- and a development-specific promoter; and an inducible promoter. The examples of the promoter include, but not limited to, a constitutive promoter 35S from cauliflower mosaic virus; a trauma-induced promoter from tomato, leucine amino peptidase ("LAP", Chao et al. (1999) Plant Physiol 120; 979-992); a chemically inducible promoter from tobacco, pathogenesis-related 1 (PR1) (induced by salicylic acid and BTH (benzothiadiazole-7-carbothiolic acid S-methyl ester)); a tomato protease inhibitor II promoter (PIN2) or an LAP promoter (both can be induced by methyl jasmonate); a heat shock promoter (U.S. Pat. No. 5,187,267); a tetracycline-inducible promoter (U.S. Pat. No. 5,057,422); a seed-specific promoter, such as millet (*Setaria italica*) seed-specific promoter pF128 (CN101063139B with a filing number of CN200710099169.7), and a seed storage protein-specific promoter (e.g., phaseolin, napin, oleosin and soybean beta conglycin promoter (Beachy et al. (1985) EMBO J. 4: 3047-3053)). They can be used separately or in combination with other plant promoters. All the references cited herein are incorporated herein by reference in their entireties. Suitable transcription terminator includes, but not limited to, a nopaline synthase terminator (NOS terminator) of *Agrobacterium*, a cauliflower mosaic virus (CaMV) 35S terminator, a tml terminator, a rbcS E9 terminator of pea and a terminator of nopaline or octopine synthase (see, e.g., Odell et al. (1985) Nature 313: 810; Rosenberg et al. (1987) Gene, 56: 125; Guerineau et al. (1991) Mol. Gen. Genet, 262: 141; Proudfoot (1991) Cell, 64: 671; Sanfacon et al. Genes Dev., 5: 141; Mogen et al. (1990) Plant Cell, 2: 1261; Munroe et al. (1990) Gene, 91: 151; Ballad et al. (1989) Nucleic Acids Res. 17: 7891; and Joshi et al. (1987) Nucleic Acid Res., 15: 9627).

A recombinant vector containing the gene expression cassette of the VdAL gene can be constructed via the existing expression vector. The plant expression vector comprises a binary *Agrobacterium tumefaciens* vector, and an expression vector that can be used for microprojectile bombardment in plant, and the like, e.g., pAHC25, pBin438, pCAMBIA1302, pCAMBIA2301, pCAMBIA1301, pCAMBIA1300, pBI121, pCAMBIA1391-Xa or pCAMBIA1391-Xb (CAMBIA Company), etc. The plant expression vector may further comprise a 3'-untranslated region of an exogenous gene, i.e., a polyadenylation signal and any other DNA fragment involved in mRNA processing or gene expression. The polyadenylation signal can lead polyadenylation to be added to the 3'-end of an mRNA precursor, e.g., the 3'-end transcribed untranslated region of gene in plasmid induced by *Agrobacterium* crown gall (Ti), e.g., nopaline synthase gene Nos, or of plant gene, e.g., soybean storage protein gene, has a similar function. When the plant expression vector is constructed via the gene of the present invention, an enhancer including a translational enhancer or a transcriptional enhancer can also be used. Enhancer region, which can be ATG initiation codon, or initiation codon in the contiguous region, etc., must be identical to the reading frame of an encoding sequence, so as to ensure correct translation of the entire sequence. The translation control signal and the initiation codon, which have a wide variety of sources, may be either natural or synthetic. The translation initiation region can be derived from a transcription initiation region or a structural gene. In order to facilitate identification and screen of the genetically modified plant cell or plant, a plant expression vector can be constructed through, e.g., addition of a gene that can be expressed in plant and encodes an enzyme producing a color or synthesizes a luminescent compound, i.e. GUS gene, luciferase gene, etc; an antibiotic marker gene, e.g., an nptII gene that confers resistance kanamycin and relevant antibiotics, a bar gene that confers resistance herbicide phosphinothricin, an hph gene that confers resistance antibiotic hygromycin, a dhfr gene that confers resistance methotrexate, an EPSPS gene that confers resistance glyphosate; an anti-chemical reagent marker gene, such as a herbicide-resistant gene; or a mannose-6-phosphate isomerase gene that provides the ability of mannose metabolism, etc. In consideration of safety of genetically modified plant, any selective marker gene may not be added, while plants are directly screened and transformed under adverse circumstances.

In the above application of the biomaterial related to the VdAL in regulating the drought resistance of plant or regulating the coloration of plant fruit, the vector may be a plasmid, cosmid, phage or virus vector. The plasmid may be vector pET42a (+).

In the above application of the biomaterial related to the VdAL in regulating the drought resistance of plant or regulating the coloration of plant fruit, the microorganism may be yeast, bacteria, algae or fungi such as *Escherichia coli*. The *Escherichia coli* may be *Escherichia coli* JM109.

In the above application of the biomaterial related to the VdAL in regulating the drought resistance of plant or regulating the coloration of plant fruit, the genetically modified plant cell line, the genetically modified plant tissue and the genetically modified plant organ may or may not include a propagating material, respectively.

In the above application of the biomaterial related to the VdAL in regulating the drought resistance of plant or regulating the coloration of plant fruit, the genetically modified plant organ may also be seeds of a genetically modified plant. The genetically modified plant may include seeds, callus, whole plant and cells.

In one embodiment of the present invention, a recombinant microorganism is obtained by the transformation of the recombinant vector comprising an expression cassette comprising the encoding gene of the VdAL is guided into *Escherichia coli* JM109. The recombinant vector is obtained by replacing a sequence between NdeI and KpnI recognition sites of a vector pET42a (+) with the DNA molecule, namely VdAL gene, represented by nucleotides $1^{st}$ to $894^{th}$ of SEQ ID No. 2 in the Sequence Listing. The recombinant vector expresses the VdAL shown in SEQ ID No. 1. The recombinant microorganism expresses the VdAL shown in SEQ ID No. 1.

In the above application of the biomaterial related to the VdAL in regulating the drought resistance of plant or regulating the coloration of plant fruit, the plant may be a plant of Monocotyledonae or a plant of Dicotyledoneae.

In order to solve the above technical problem, the present invention further provides a method for improving the drought resistance of a plant or promoting coloration of a plant fruit.

The present method for improving the drought resistance of a plant or promoting the coloration of a plant fruit includes a step of applying the VdAL, the biomaterial or the biological agent to a target plant, so as to improve the product quality of the target plant. The active ingredient of the biological agent is the VdAL or the biomaterial.

In the above method for improving the drought resistance of plant or promoting the coloration of plant fruit, the biological agent can be prepared by method 1). Said method 1) is that the recombinant microorganism is cultivated to express the encoding gene of the VdAL is expressed to obtain the biological agent.

In the above method for improving the drought resistance of plant or promoting the coloration of plant fruit, said method 1) may specifically comprise 11) and 12) as follows:

11) cultivating the recombinant microorganism to express the encoding gene to obtain culture of recombinant microorganism expressing the protein; and 12) disrupting thalli of the microorganism culture to obtain a biological agent.

In the above method for improving the drought resistance of plant or promoting the coloration of plant fruit, said method 1) may further include a step of drying the biological agent.

In the above method for improving the drought resistance of plant or promoting the coloration of plant fruit, the encoding gene may be the nucleic acid molecule of B1).

In one embodiment of the present invention, the recombinant microorganism is obtained by the transformation of the recombinant vector comprising an expression cassette comprising the encoding gene of the VdAL into *Escherichia coli* JM109. The recombinant vector is obtained by replacing a sequence between NdeI and KpnI recognition sites of a vector pET42a (+) with the DNA molecule, namely VdAL gene represented by nucleotides $1^{st}$ to $894^{th}$ nucleotides of SEQ ID No. 2. The recombinant vector expresses the VdAL shown in SEQ ID No. 1. The recombinant microorganism expresses the VdAL shown in SEQ ID No. 1.

In the above method for improving the drought resistance of plant or promoting the coloration of plant fruit, the step of applying the VdAL, the biomaterial or the biological agent to a target plant may specifically be a step of applying the VdAL, the biomaterial or the biological agent to leaves of the target plant, e.g., spraying the VdAL, the biomaterial or the biological agent to the target plant; or treating seeds of the target plant with the VdAL, the biomaterial or the biological agent, e.g., soaking the seeds of the target plant into a liquid agent of the VdAL, the biomaterial or the biological agent. The liquid agent of the VdAL, the biomaterial or the biological agent may be the liquid obtained by directly dissolving or suspending the VdAL, the biomaterial or the biological agent into clear water. The quantity of the VdAL, the biomaterial or the biological agent applied to the target plant may be determined according to the species and/or growth phase of the target plant.

In the above method for improving the drought resistance of a plant or promoting the coloration of plant fruit, the plant is a plant of Monocotyledonae or a plant of Dicotyledoneae.

In order to solve the above technical problem, the present invention further provides an application of a biological agent in improving the drought resistance of a plant or promoting coloration of a plant fruit.

In the above application of the biological agent in improving the drought resistance of a plant or promoting the coloration of plant fruit, the plant is a plant of Monocotyledonae or a plant of Dicotyledoneae.

In the above description, the effects of the VdAL or the biological agent on different plants may be different due to different concentrations thereof. When the VdAL or the biological agent is applied, the concentration of the VdAL or the biological agent can be adjusted according to a crop or a variety thereof and the purpose of applying the VdAL or the biological agent.

In an embodiment of the present invention, when the mass percentage content of the biological agent is 0.2-4%, drought resistance of wheat can be improved. The liquid obtained by diluting the biological agent 3000-5000 times can promote coloration of cherry or grape.

BRIEF DESCRIPTION OF THE DRAWINGS

FIG. 1 shows the VdAL appearance and a western-blot detection result of the VdAL, wherein A is the VdAL appearance; B is the western-blot detection result of the VdAL, fan represents fine powder entering the air outlet during drying process of the sample, and main tower represents normal powder during drying process of the sample.

FIG. 2 shows that the VdAL can promote vegetative growth of watermelon, wherein CK represents untreated watermelon, and VdAL represents watermelon treated with the VdAL.

FIG. 3 shows that the VdAL can promote fruit setting and expansion of cucumber, wherein CK represents untreated cucumber, 1/300 represents cucumber treated with 300 times diluted VdAL, 1/600 represents cucumber treated with 600 times diluted VdAL, and 1/900 represents cucumber treated with 900 times diluted VdAL.

FIG. 4 shows the growth vigor of cucumber with different treatments, wherein CK represents untreated cucumber, and 1/300 represents cucumber treated with 300 times diluted VdAL.

FIG. 5 shows the situation of aging of cucumber with different treatments, wherein CK represents untreated cucumber, and 1/2000 represents cucumber treated with 2000 times diluted VdAL.

FIG. 6 shows the situation of fruit setting of cherry tomato with different treatments, wherein CK represents untreated cherry tomatoes, and 1/2000 represents cherry tomatoes treated with 2000 times diluted VdAL.

Figure 10:
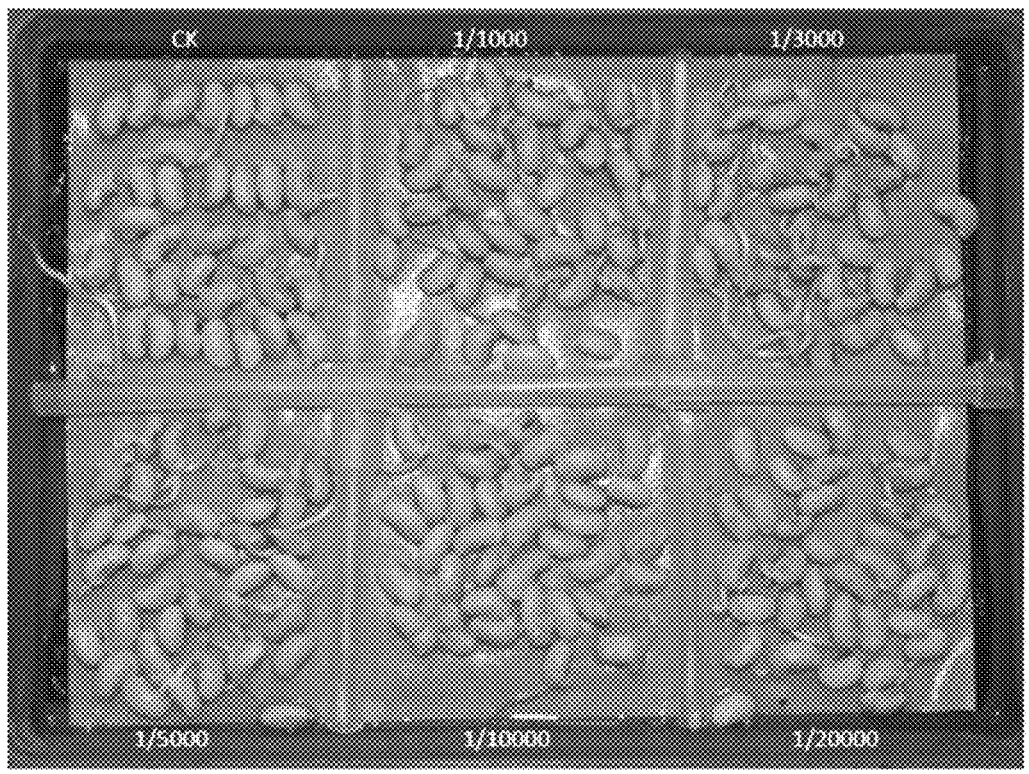

FIG. 10 shows the situation of germination of soybean seed with different treatments, wherein CK represents untreated soybean seeds, 1/1000 represents soybean seeds treated with 1000 times diluted VdAL, 1/3000 represents soybean seeds treated with 3000 times diluted VdAL, 1/5000 represents soybean seeds treated with 5000 times diluted VdAL, 1/10000 represents soybean seeds treated with 10000 times diluted VdAL, and 1/20000 represents soybean seeds treated with 20000 times diluted VdAL.

Figure 11:
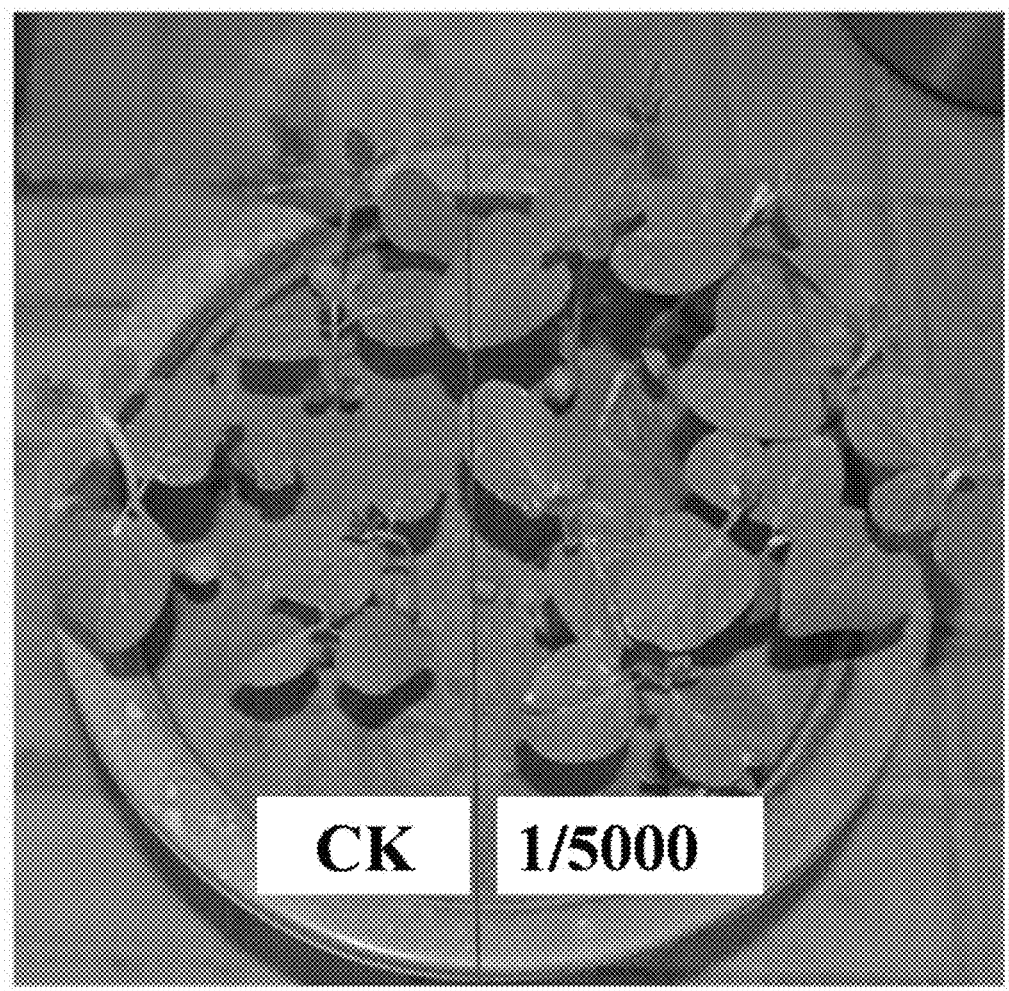

FIG. 11 shows the growth situation of soybean seedling with different treatments, wherein CK represents untreated soybean seedlings, and 1/5000× represents soybean seedlings treated with 5000 times diluted VdAL.

Figure 12:
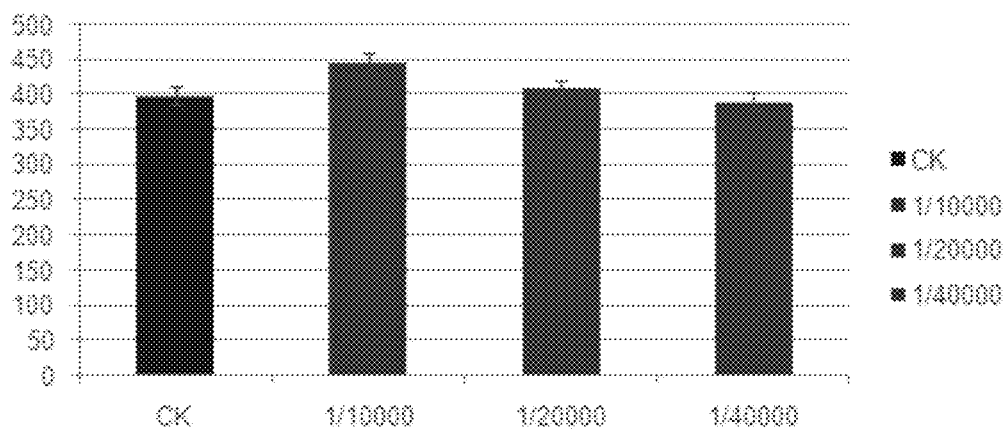

FIG. 12 shows the yield per MU of rice treated with the VdAL.

Figure 13:

FIG. 13 shows the growth situation of each group of wheat under 7-day water-control.

Figure 14:
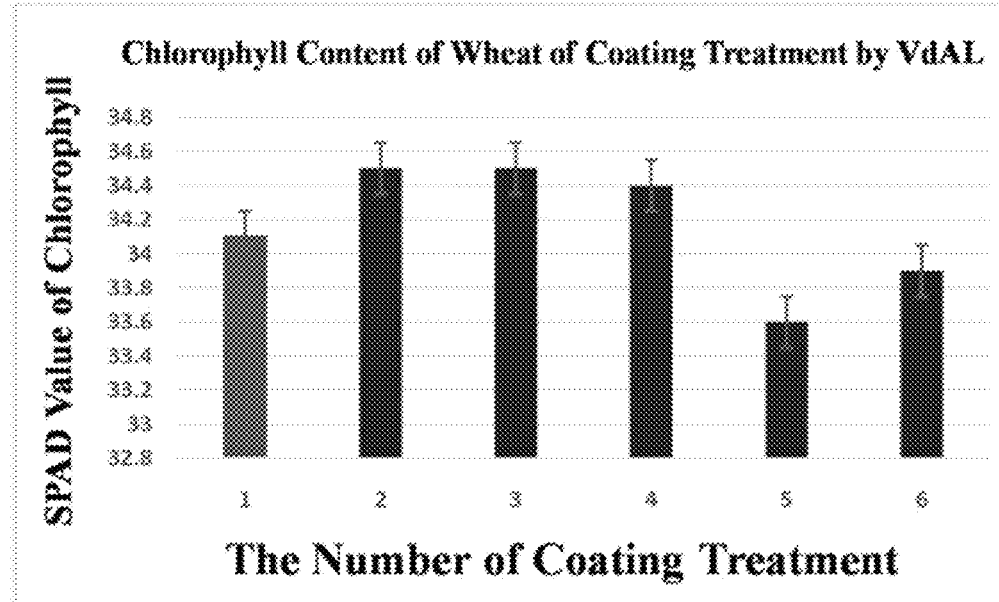

FIG. 14 shows the chlorophyll content of leaves of each group of wheat.

Figure 15:
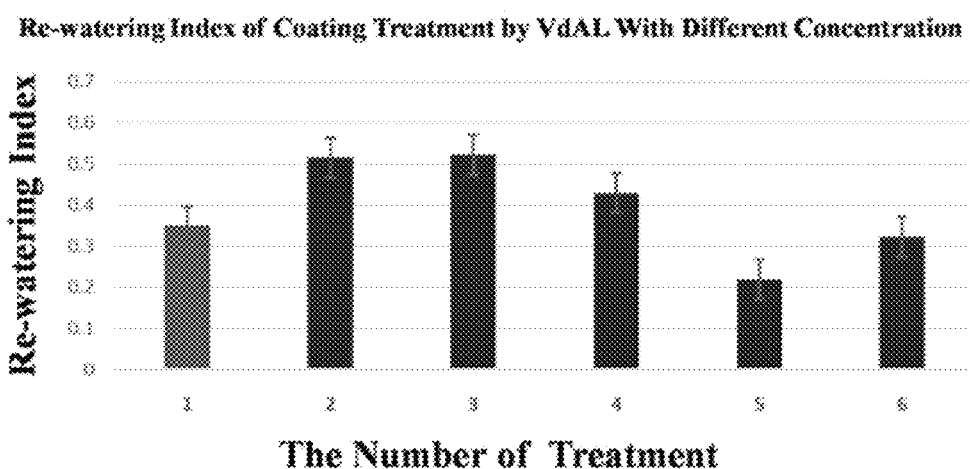

FIG. 15 shows re-watering indexes of each group of wheat.

Figure 16:
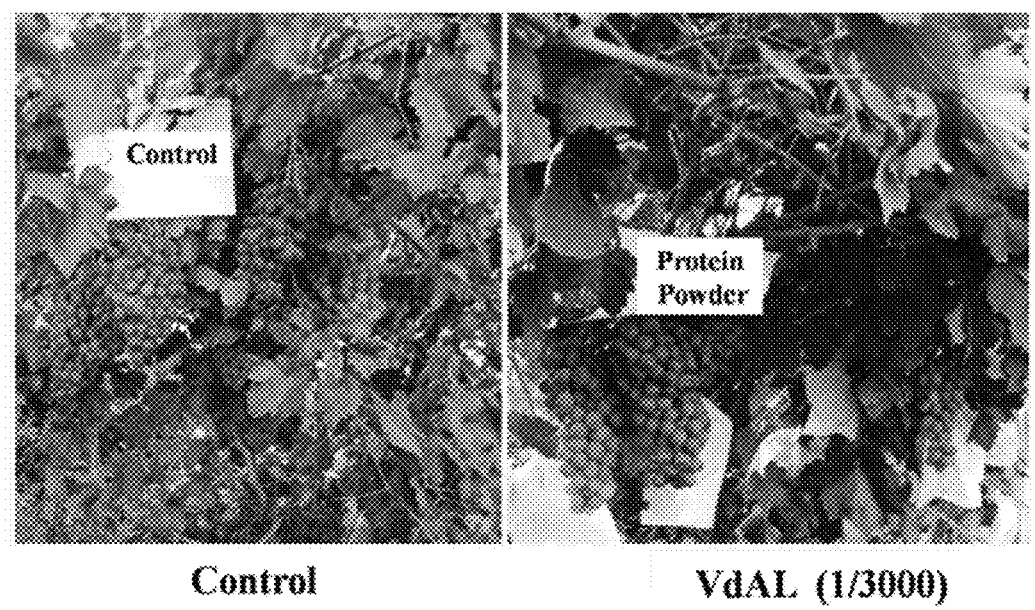

FIG. 16 shows grape with two different treatments.

Figure 17:

FIG. 17 shows cherries with two different treatments.

Figure 18:
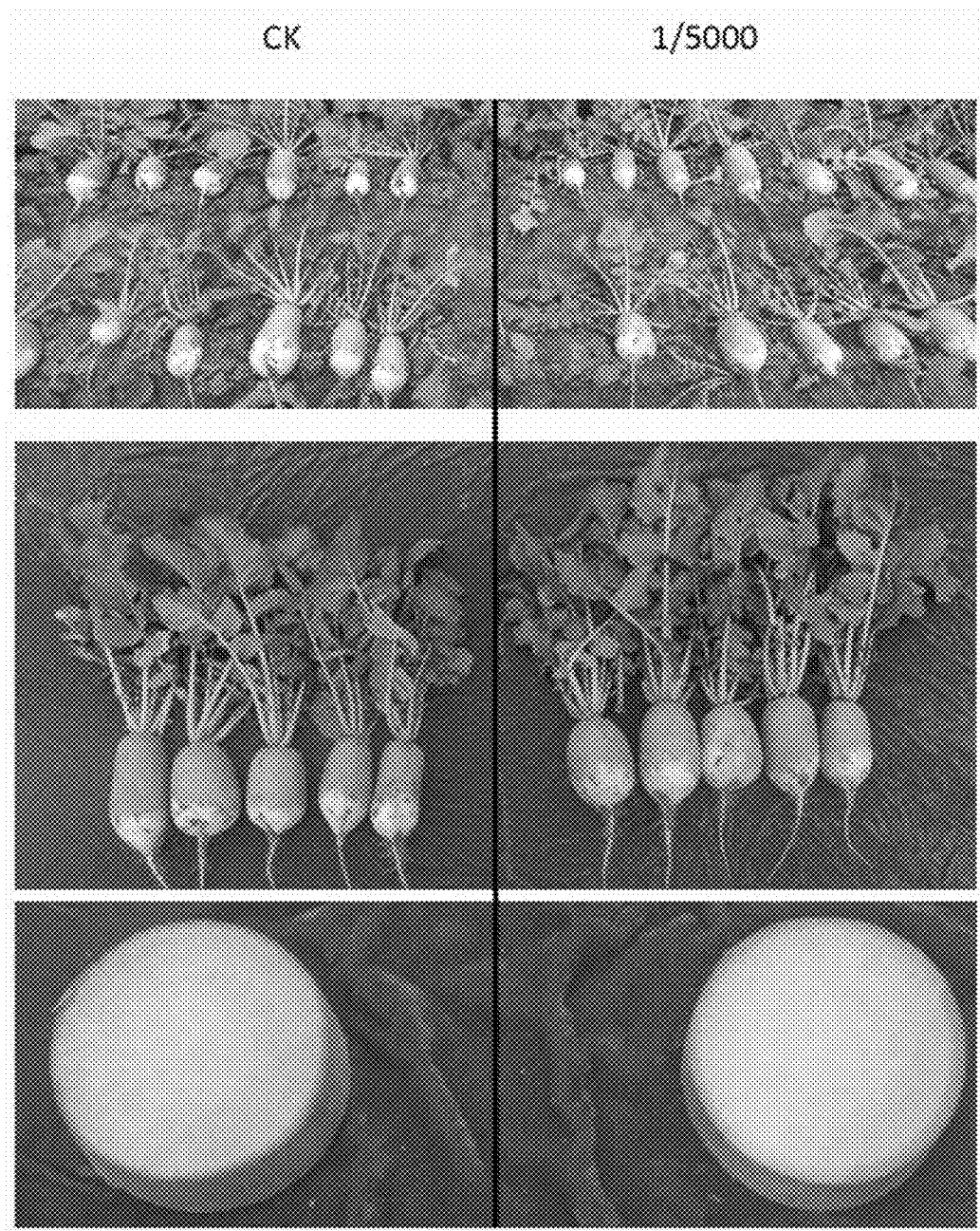

FIG. 18 shows appearance of can-like radish in two treatments.

In the context, 1/300, 1/600, 1/900, 1/1000, 1/200, 1/250, 1/3000, 1/4000, 1/5000, 1/6000, 1/7500, 1/10000, 1/20000 and 1/40000 times VdAL respectively represent 300 times diluted VdAL, 600 times diluted VdAL, 900 times diluted VdAL, 1000 times diluted VdAL, 2000 times diluted VdAL, 2500 times diluted VdAL, 3000 times diluted VdAL, 4000 times diluted VdAL, 5000 times diluted VdAL, 6000 times diluted VdAL, 7500 times diluted VdAL, 10000 times diluted VdAL, 20000 times diluted VdAL, and 40000 times diluted VdAL.

DETAILED DESCRIPTION OF THE EMBODIMENTS

The present invention will be described in further detail with reference to specific examples, which are provided for illustration of the present invention only, but not intended to limit the scope of the present invention.

Experimental methods indicated in the following examples are conventional approaches, unless otherwise specified.

Materials, agents and the like used in the following examples are all commercially available, unless otherwise specified.

*Escherichia coli* JM109 in the following examples is a product of Beijing Solarbio Science & Technology Co., Ltd. The catalog number thereof is C1300.

Vector pET42a (+) in the following examples is a product of Beijing SinaSun Biotechnology Co., Ltd. The catalog number thereof is S 18-16.

Xinluzao No. 58 in the following examples is a product of Xinjiang Jinmian Seed Industry Science & Technology Co., Ltd. In addition, Lu No. 30, 616, Lu No. 25 and Luyanmian No. 24 are products of Shandong Nongxing Seed Industry Co., Ltd.

Variety of watermelon, Jinlidu, in the following examples is a product of Shouguang Jishan Commercial and Trading Co., Ltd.

Zhongmai 816 in the following examples is a product of Beijing Longshengyuan Science & Technology Development Co., Ltd.

Variety of tomato, Fux, in the following examples is a product of Shouguang Jinpeng Seed Industry Co., Ltd.

Variety of green-stem cabbage, Huali FI, in the following examples is a product of Shanghai Hongqiao Tianlong Seed Industry Co., Ltd.

Variety of cucumber, Jinza No. 1, in the following examples is a product of Shandong Nongxing Seed Industry Co., Ltd.

Variety of cherry tomato, Jingdan No. 2, in the following examples is a product of Beijing Beinong Lvheng Science & Technology Development Co., Ltd.

Variety of strawberry, Fengxiang, in the following examples is a product of Beijing Beinong Luheng Sci-Tech Development Co., Ltd.

Variety of melon, Super Cuibaoxiang, in the following examples is a product of Jinan Ruimao Agricultural Science & Technology Development Co., Ltd.

Variety of sweet pepper, Ruiyou 816, in the following examples is a product of Jinan Ruimao Agricultural Science & Technology Development Co., Ltd.

Variety of soybean, King of China soybean, in the following examples is a product of Jinan Ruimao Agricultural Science & Technology Development Co., Ltd.

Variety of rice, Nongda 502, in the following examples is a product of Beijing Beinong Luheng Sci-Tech Development Co., Ltd.

Example 1 Preparation of the Agent of VdAL

The agent of VdAL was developed by China Agricultural University, and produced by Shandong Huimin Huhao Biotechnology Co., Ltd.

1. Construction of Recombinant Vector and Recombinant Bacterium

Figure 1:
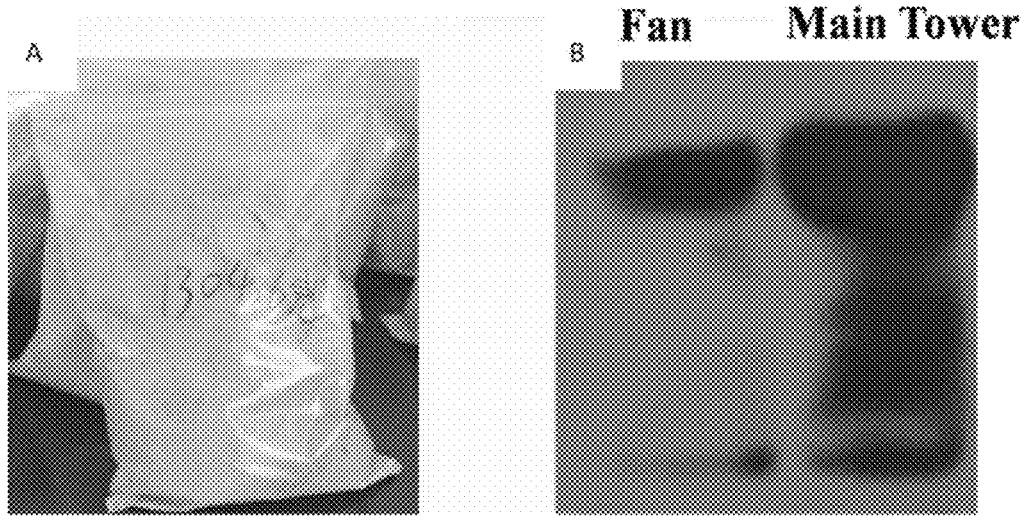
Figure 2:
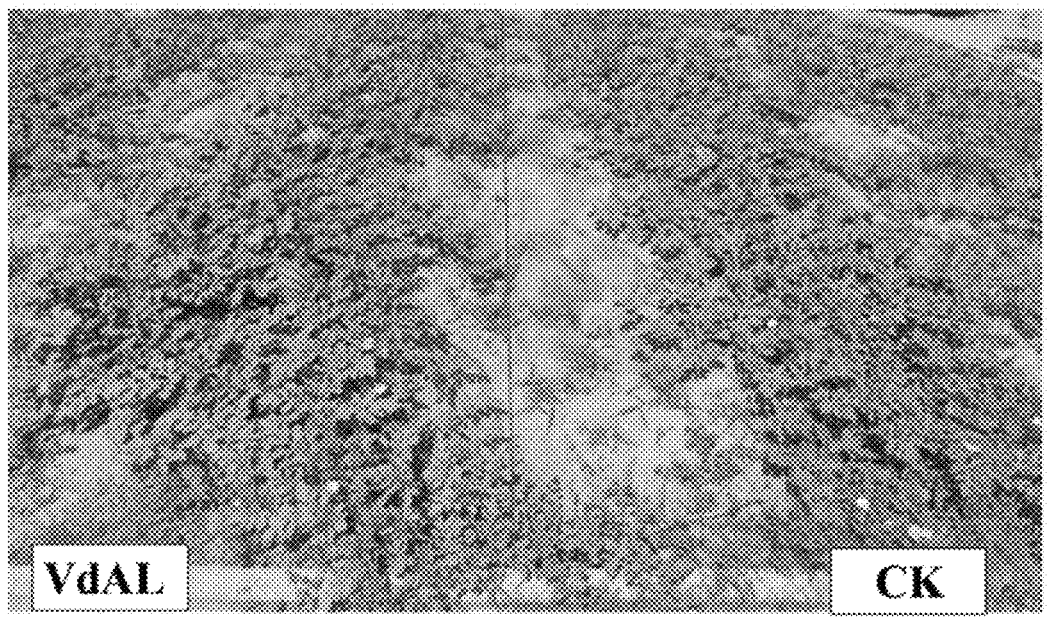
Figure 3:
Figure 4:
Figure 5:
Figure 6:
Figure 7:
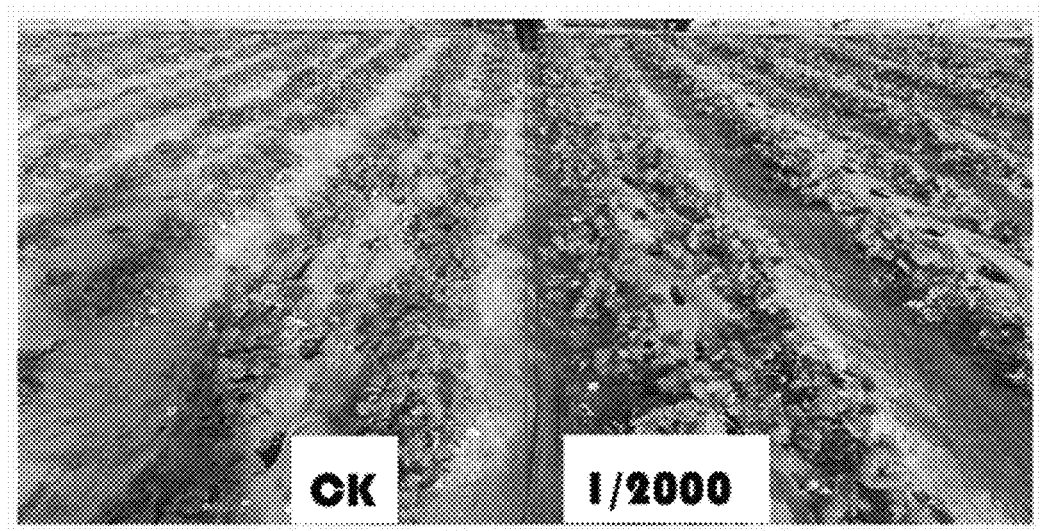
FIG. 7 shows strawberries with different treatments, wherein CK represents untreated strawberries, and 1/2000 represents strawberries treated with 2000 times diluted VdAL.

The DNA molecule represented by nucleotides 1st to 894th of SEQ ID No. 2 in the Sequence Listing, i.e. the VdAL gene, was artificially synthesized. A sequence between NdeI and KpnI recognition sites of a vector pET42a (+) was replaced with the DNA molecule represented by nucleotides $1^{st}$ to $894^{th}$ of SEQ ID No. 2 in the Sequence Listing, i.e., the VdAL gene, while other sequences of the pET42a (+) remained unchanged. A recombinant vector was thus obtained. The obtained recombinant vector was named pET42a-VdAL. The recombinant vector pET42a-VdAL expresses the VdAL protein shown in SEQ ID No. 1 in the Sequence Listing.

SEQ ID No. 2 is composed of 894 nucleotides encoding the amino acid sequence shown in SEQ ID No. 1.

The pET42a-VdAL was transformed into *Escherichia coli* JM109 to obtain recombinant bacterium. The obtained recombinant bacterium was named JM109-pET42a-VdAL. JM109-pET42a-VdAL expresses the protein shown in SEQ ID No. 1.

2. Preparation of the Agent of VdAL

JM109-pET42a-VdAL was fermented at 37° C. until OD value was 0.6, so that a pre-fermented liquid was obtained.

IPTG was added into the pre-fermented liquid at the concentration of 1 mM to obtain induced liquid. The induced liquid was fermented for 6 hours at 25° C. to obtain fermented liquid. The fermented liquid was centrifuged. The supernate was removed. The obtained thalli pellet was disrupted. Then a dry powder agent (A in FIG. 1) was obtained at 150° C. through spray drying, named as the agent of VdAL.

The VdAL in the agent of VdAL was detected by western-blot method. The primary antibody was anti-VdAL antibody which was polyclonal antibody obtained by using the protein shown in SEQ ID No. 2 as an immunogen. The result showed that the agent of VdAL comprised the VdAL protein (B in FIG. 1) with a concentration of 7.28 mg/g.

The agent of VdAL was dissolved into clear water to obtain liquids having the VdAL protein at the concentrations of 10 g/3 kg, 10 g/6 kg, 10 g/9 kg, 1 g/kg, 1 g/2 kg, 1 g/2.5 kg, 1 g/3 kg, 1 g/4 kg, 1 g/5 kg, 1 g/6 kg, 1 g/7.5 kg, 1 g/10 kg, 1 g/20 kg and 1 g/40 kg, respectively. These liquids were respectively named as 300 times diluted VdAL, 600 times diluted VdAL, 900 times diluted VdAL, 1000 times diluted VdAL, 2000 times diluted VdAL, 2500 times diluted VdAL, 3000 times diluted VdAL, 4000 times diluted VdAL, 5000 times diluted VdAL, 6000 times diluted VdAL, 7500 times diluted VdAL, 10000 times diluted VdAL, 20000 times diluted VdAL and 40000 times diluted VdAL.

Example 2 the Agent of VdAL can Promote the Growth of Cotton

1. The Agent of VdAL can Promote Germination of Cotton Seeds

The seeds of variety, Xinluzao No. 58, were soaked into 5000 times diluted VdAL, 7500 times diluted VdAL and 10000 times diluted VdAL in Example 1 and clear water for 24 hours, respectively. Germination experiment was performed in big flower pots. The temperature was 25° C. The germination rate of cotton seeds was statistically analyzed in the 8$^{th}$ day after seeding. 100 seeds were treated in every treatment. The experiment was repeated three times.

The results showed that the average germination rates of cotton were 74.00%, 75.50%, 71.00% and 70.23%, respectively, after the cotton seeds were treated with the 5000 times diluted VdAL, the 7500 times diluted VdAL, the 10000-times diluted VdAL and clear water. The average germination rates of cotton after the cotton seeds were treated with the 5000 times diluted VdAL, the 7500 times diluted VdAL and the 10000 times diluted VdAL are respectively 1.05 times, 1.08 times and 1.01 times that after the cotton seeds were treated with clear water. This indicated that the agent of VdAL could improve the germination rate of cotton seeds, and its capability of improving the germination rate of cotton seeds was changed with the change of the concentration of the agent of VdAL.

2. The Agent of VdAL can Improve the Yield of Cotton

Experiment I

Field experiment was designed as follows. The experiment adopted randomized block design. Three replicate blocks were provided. Each replicate block was randomly provided with nine treatment areas which were respectively VdAL treatment area I of Lu No. 30, VdAL treatment area II of Lu No. 30, contrast treatment area of Lu No. 30, VdAL treatment area I of 616. VdAL treatment area II of 616, contrast treatment area of 616, VdAL treatment area I of Lu No. 25, VdAL treatment area II of Lu No. 25 and contrast treatment area of Lu No. 25. The area of each treatment area was 0.2 mu.

At seedling stage, and blossoming and boll-forming early stage, Lu No. 30 in VdAL treatment area I of Lu No. 30 was respectively treated according to the following method. A 3000 times diluted VdAL of Example 1 with 45-50 kg per mu was sprayed to cotton leaves by the means of top spraying (mechanical spraying) to obtain Lu No. 30 treated with the 3000 times diluted VdAL. It was sprayed once at seedling stage, and blossoming and boll-forming early stage respectively. The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of Lu No. 30 of VdAL treatment area I, the 3000 times diluted VdAL was replaced with a 5000 times diluted VdAL to treat Lu No. 30 of VdAL treatment area II. Other steps remained unchanged. Thus Lu No. 30 treated with the 5000 times diluted VdAL was obtained.

According to the treatment method of Lu No. 30 of VdAL treatment area I, the 3000 times diluted VdAL was replaced with clear water to treat Lu No. 30 of contrast treatment area. Other steps remained unchanged. Untreated Lu No. 30 was obtained.

According to the treatment method of Lu No. 30 of VdAL treatment area I, 616 of VdAL treatment area I and Lu No. 25 of VdAL treatment area I were respectively treated. Other steps remained unchanged. 616 and Lu No. 25 treated with the 3000 times diluted VdAL were obtained, respectively.

According to the treatment method of Lu No. 30 of VdAL treatment area I, the 3000 times diluted VdAL was replaced with a 5000 times diluted VdAL to treat 616 of VdAL treatment area II and Lu No. 25 of VdAL treatment area II, respectively. Other steps remained unchanged. 616 and Lu No. 25 treated with the 5000 times diluted VdAL were obtained, respectively.

According to the treatment method of Lu No. 30 of VdAL treatment area I, the 3000 times diluted VdAL was replaced with clear water to treat 616 of contrast treatment area and Lu No. 25 of contrast treatment area respectively. Other steps remained unchanged. Untreated 616 and Untreated Lu No. 25 were obtained, respectively.

The cotton yield before first frost, cotton yield after first frost and total yield, of Lu No. 30 treated with the 3000 times diluted VdAL, Lu No. 30 treated with the 5000 times diluted VdAL, untreated Lu No. 30, 616 treated with the 3000 times diluted VdAL, 616 treated with the 5000 times diluted VdAL, untreated 616. Lu No. 25 treated with the 3000 times diluted VdAL, Lu No. 25 treated with the 5000 times diluted VdAL and untreated Lu No. 25 were statistically analyzed, respectively. The results were shown in Table 2.

TABLE 2

The average yield of cotton in different treatments

| Variety | Treatment | Cotton yield before first frost Yield (kg/mu) | Cotton yield before first frost Increasing rate (%) | Cotton yield after first frost Yield (kg/mu) | Total yield Total Yield | Total yield Increasing rate (%) |
|---|---|---|---|---|---|---|
| Lu No. 30 | Treatment 1 | 211.36 | 19.48 | 4.31 | 215.67 | 17.04 |
|  | Treatment 2 | 214.50 | 21.25 | 6.63 | 221.13 | 20.00 |
|  | CK | 176.90 | — | 7.37 | 184.28 | — |
| 616 | Treatment 1 | 150.33 | −2.65 | 4.65 | 154.98 | −3.15 |
|  | Treatment 2 | 183.86 | 19.06 | 7.66 | 191.52 | 19.69 |
|  | CK | 154.42 | — | 5.60 | 160.02 | — |
| Lu No. 25 | Treatment 1 | 157.05 | 1.05 | 5.70 | 162.75 | 0 |
|  | Treatment 2 | 180.87 | 16.37 | 10.53 | 191.39 | 17.60 |
|  | CK | 155.43 | — | 7.32 | 162.75 | — |

Note:
Treatment 1 represented the treatment with the 3000 times diluted VdAL, Treatment 2 represented the treatment with the 5000 times diluted VdAL, and CK represented untreatment (i.e., treatment with clear water).

The results showed that the VdAL with a proper concentration could improve the yield of cotton. The cotton yield before first frost was improved by 19.48% and the total yield was improved by 17.04%, after Lu No. 30 was treated with the 3000 times diluted VdAL. The cotton yield of Lu No. 30 before first frost was improved by 21.25% and the total yield thereof was improved by 20.00%, the cotton yield of 616 before first frost was improved by 19.06% and the total yield thereof was improved by 19.69%, and the cotton yield of Lu No. 25 before first frost was improved by 16.37% and the total yield thereof was improved by 17.60%, after cotton was treated with the 5000 times diluted VdAL.

Experiment II

Field experiment was designed as follows. The experiment adopted randomized block design. Three replicate blocks were provided. Each replicate block was randomly provided with four treatment areas which were respectively VdAL treatment area I, VdAL treatment area II, VdAL treatment area III and contrast treatment area. The area of each treatment area was 10 mu.

At seedling stage, and blossoming and boll-forming early stage, Luyanmian No. 24 in VdAL treatment area I was respectively treated according to the following method. A 3000 times diluted VdAL of Example 1 with 45-50 kg per mu was sprayed to cotton leaves by the means of top spraying (mechanical spraying) to obtain Luyanmian No. 24 treated with the 3000 times diluted VdAL. The operation was performed at the speed of about 6 kilometers per hour. The agent of VdAL was sprayed once at seedling stage, and blossoming and boll-forming early stage respectively. The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area I, the 3000 times diluted VdAL was replaced with a 5000 times diluted VdAL to treat VdAL treatment area II. Other steps remained unchanged. Luyanmian No. 24 treated with the 5000 times diluted VdAL was obtained.

According to the treatment method of VdAL treatment area I, the 3000 times diluted VdAL was replaced with a 10000 times diluted VdAL to treat VdAL treatment area III. Other steps remained unchanged. Luyanmian No. 24 treated with the 10000 times diluted VdAL was obtained.

According to the treatment method of VdAL treatment area I, the 3000 times diluted VdAL was replaced with clear water to treat contrast treatment area. Other steps remained unchanged. Untreated Luyanmian No. 24 was obtained.

Plant number per mu, the number of boll setting of individual plant, total number of the boll per mu, the weight of single boll, ginning outturn and the yield per mu, of Luyanmian No. 24 in each treatment were statistically analyzed. Means of each item and increasing rates compared with the contrast were shown in Table 3 and Table 4.

TABLE 3

Means and increasing rates of each item of Luyanmian No. 24 in each treatment

| Items Treatment | Per mu plants Plant number per mu | Per mu plants Increasing rate (%) | Boll setting of individual plant the number of boll setting of individual plant | Boll setting of individual plant Increasing rate (%) | Total bolls per mu Total number of the boll per mu | Total bolls per mu Increasing rate(%) |
|---|---|---|---|---|---|---|
| Treatment 1 | 7901 | −2.2 | 9.2 | +4.5 | 72283 | +1.98 |
| Treatment 2 | 8184 | +1.4 | 9.1 | +3.41 | 74006 | +4.41 |

TABLE 3-continued

Means and increasing rates of each item of Luyanmian No. 24 in each treatment

| | Per mu plants | | Boll setting of individual plant | | Total bolls per mu | |
|---|---|---|---|---|---|---|
| Items Treatment | Plant number per mu | Increasing rate (%) | boll setting of individual plant | Increasing rate (%) | Total number of the boll per mu | Increasing rate(%) |
| Treatment 3 | 8154 | +1.0 | 8.7 | −1.14 | 71011 | +0.18 |
| CK | 8072 | / | 8.8 | / | 70880 | / |

Note:
Treatment 1 represented the treatment with the 3000 times diluted VdAL, Treatment 2 represented the treatment with the 5000 times diluted VdAL, Treatment 3 represented the treatment with the 10000 times diluted VdAL, and CK representsuntreated (i.e., treated with clear water).

TABLE 4

Means and increasing rates of each item of Luyanmian No. 24 in each treatment

| | Weight of single boll | | Ginning outturn | | Yield per mu | |
|---|---|---|---|---|---|---|
| Items Treatment | Weight of single boll (g) | Increasing rate (%) | Ginning outturn (%) | Increasing rate (%) | Yield per mu (kg/mu) | Increasing rate (%) |
| Treatment 1 | 5.4 | 0 | 41.2 | 0.24 | 392 | +1.76 |
| Treatment 2 | 5.5 | +1.9 | 41.3 | 0.49 | 405.3 | +5.22 |
| Treatment 3 | 5.4 | 0 | 41.2 | 0.24 | 384.4 | −0.21 |
| CK | 5.4 | / | 41.1 | / | 385.2 | / |

Note:
Treatment 1 represented the treatment with the 3000 times diluted VdAL, Treatment 2 represented the treatment with the 5000 times diluted VdAL, Treatment 3 represented the treatment with the 10000 times diluted VdAL, and CK represented untreatment (i.e., the treatment with clear water).

The results showed that the VdAL with a proper concentration could improve the number of plant per mu, the number of boll setting of individual plant, total number of boll per mu, the weight of single boll, ginning outturn and the yield per mu of cotton. The number of boll setting of individual plant, total number of boll per mu, ginning outturn and the yield per mu were increased, and the increasing rates were 4.5%, 1.98%, 0.24% and 1.76%, respectively, after cotton was treated with the 3000 times diluted VdAL. The number of plant per mu, the number of boll setting of individual plant, total number of boll per mu, the weight of single boll, ginning outturn and the yield per mu were increased, and the increasing rates were 1.4%, 3.41%, 4.41%, 1.9%, 0.49% and 5.22% respectively, after cotton was treated with the 5000 times diluted VdAL. The increasing rates of each item, when being treated with the 10000 times diluted VdAL, was lower than that of being treated with the 3000 times diluted VdAL and the 5000 times diluted VdAL. It indicated that the quality and the yield of cotton could be improved by applying VdAL with a proper concentration.

Example 3 the Agent of VdAL can Improve the Quality and Yield of Watermelon

Field experiment was designed as follows. The experiment adopted randomized block design. Three replicate blocks were provided. Each replicate block was randomly provided with two treatment areas, which were respectively VdAL treatment area and contrast treatment area. The area of each treatment area was 0.2 mu.

The variety of watermelon, Jinlidu, in VdAL treatment area was treated according to the following method. A 2000 times diluted VdAL of Example 1 with 30 kg per mu was sprayed to watermelon leaves by the means of top spraying (mechanical spraying) to obtain watermelon treated with the 2000 times diluted VdAL. It was sprayed at the seedling stage of watermelon for the first time, and sprayed once more 15 days after the first time. It was sprayed two times in total. The spraying was performed on morning or at evening, and preferably not at the high temperature period at noon. The agent of VdAL was preferably not mixed with pesticides and fertilizers at spraying. The agent of VdAL should be sprayed once again if it rained within 2 hours after being sprayed.

According to the treatment method of VdAL treatment area, the 2000 times diluted VdAL was replaced with clear water to treat the contrast treatment area. Other steps remained unchanged. Untreated watermelons were obtained.

The results showed that the agent of VdAL had a promoting effect on vegetative growth and fruit setting of watermelon (FIG. 2). The yields of watermelon in different treatment areas were statistically analyzed. The results showed that the fruit number of individual plant was 1.43±0.5 and the yield was 5200.2±500 kg/mu after the watermelon was treated with VdAL of 2000 times dilution, whereas the fruit number of individual plant of untreated watermelon was 1.21±0.5 and the yield of untreated watermelon was 3898.2500 kg/mu. Compared with the untreated watermelon, the fruit number of individual plant of watermelon treated with the agent of VdAL was improved by 18.2%, and the yield of watermelon treated with the agent of VdAL was improved by 33.4%.

The water content, dry matter content, Vc content, soluble sugar content, titratable acid content, soluble solid content, peel thickness, protein content and coarse fiber content (Table 5), as well as the content of trace elements Ca, Cu, Fe, K, Mg, Mn, Na, P and Zn (Table 6), of watermelon with different treatments were respectively determined at the maturation stage of watermelon. The water content and the dry matter content (the percentage of dry matters in watermelon to fresh watermelon) were determined after the watermelon was dried. The Vc content was determined by a 2,6-dichlorophenol indophenol titration method. The soluble sugar content was determined by anthrone colorimetry. The titratable acid content was determined by colorimetry. The soluble solid content and the protein content were determined by spectrophotometry. The coarse fiber content was determined by the determination of crude fiber by Weende method. The content of trace elements Ca, Cu, Fe, K, Mg, Mn, Na, P and Zn were determined in each case by using trace element analyzer.

TABLE 5

Average content of each index of watermelon in different treatments

| Index | Untreated | Treated by the VdLA |
|---|---|---|
| Water content (%) | 90.22 | 91.43 |
| Dry matter content (%) | 9.78 | 8.57 |
| Vc(mg/100 g) | 12.1 | 18.2 |
| Soluble sugar (%) | 6.83 | 7.44 |
| Titratable acid (%) | 0.09 | 0.09 |
| Soluble solid (%) | 9.1 | 9.1 |
| Peel thickness (cm) | 0.97 | 1.23 |
| Protein (% DW) | 5.54 | 6.33 |
| Protein(% FW) | 0.54 | 0.54 |
| Coarse fiber(% DW) | 2.06 | 2.02 |
| Coarse fiber(% FW) | 0.2 | 0.17 |

TABLE 6

Average content of each trace element of watermelon in different treatments

| No. | Index | Untreated | treated by the VdAL |
|---|---|---|---|
| 1 | Water content (%) | 90.22 | 91.43 |
| 2 | Ca (mg/L) | 20.13 | 22.70 |
| 3 | Ca content (mg/100 gFw) | 9.83 | 9.71 |
| 4 | Cu (mg/L) | 0.13 | 0.15 |
| 5 | Cu content (mg/100 gFw) | 0.06 | 0.06 |
| 6 | Fe (mg/L) | 0.50 | 0.60 |
| 7 | Fe content (mg/100 gFw) | 2.50 | 2.98 |
| 8 | K (mg/L) | 158.00 | 184.00 |
| 9 | K content (mg/100 gFw) | 77.19 | 78.64 |
| 10 | Mg (mg/L) | 22.27 | 22.50 |
| 11 | Mg content (mg/100 gFw) | 10.88 | 9.63 |
| 12 | Mn (mg/L) | 0.10 | 0.12 |
| 13 | Mn content (mg/100 gFw) | 0.05 | 0.05 |
| 14 | Na (mg/L) | 7.20 | 7.35 |
| 15 | Na content (mg/100 gFw) | 3.52 | 3.14 |
| 16 | P (mg/L) | 18.30 | 20.13 |
| 17 | P content (mg/100 gFw) | 8.93 | 8.65 |
| 18 | Zn (mg/L) | 0.25 | 0.30 |
| 19 | Zn content (mg/100 gFw) | 0.12 | 0.13 |

Note:
The content of each trace element in lines 3, 5, 7, 9, 11, 13, 15, 17 and 19 referred to the mass of each trace element of fresh watermelon per liter. The content of each trace element in lines 2, 4, 6, 8, 10, 12, 14, 16 and 18 referred to the content of each trace element in fresh watermelon.

The results showed that the water content of watermelon was slightly increased by 1.34%, the Vc content was remarkably improved by 50.41%, the soluble sugar content was improved by 8.88%, the protein content of dry matters was improved by 14.2%, the protein content of fresh watermelon was improved by 0.62%, the titratable acid content and the soluble solid content remained unchanged, the dry matter content reduced by 12.4%, and the coarse fiber content reduced slightly after watermelon was treated with the agent of VdAL. It indicated that the contents of main nutrients in watermelon were increased, while the acidity was not significantly increased, and the dry matter content and the coarse fiber content decreased respectively, after watermelon was treated with the agent of VdAL, so that the palatability of watermelon was improved. After watermelon was treated with the agent of VdAL, the masses of Ca, Cu, Fe, K, Mg, Mn, Na, P and Zn in fresh watermelon per liter were increased by 12.75%, 16.54%, 19.21%, 16.46%, 1.05%, 20.45%, 2.13%, 10.02% and 19.73% respectively, and the mass contents of Cu, Fe, K, Mn and Zn in fresh watermelon were increased by 2.09%, 19.09%, 1.88%, 5.72% and 5.07% respectively. It indicated that the agent of VdAL could significantly improve the contents of trace elements Cu. Fe, K, Mn and Zn, which was beneficial to human body, in watermelon. The above experiment proved that the agent of VdAL could improve the quality of watermelon.

Example 4 the Agent of VdAL can Promote the Growth of Wheat and Improve the Yield of Wheat I. The Agent of VdAL can Promote the Germination and Vegetative Growth of Wheat Experiment I The seeds of variety, Zhongmai 816, were respectively soaked into a 1000 times diluted VdAL, a 2000 times diluted VdAL, a 5000 times diluted VdA and a 10000 times diluted VdAL of Example 1 and clear water for 12 hours, and then accelerate germination for 96 hours at 25° C. in germination boxes, in which two layers of sterile filter paper wetted with sterile water were spread. The germination rate of the wheat seeds was statistically analyzed. The germination standard of the wheat seeds was that the bud length was equal to or more than half of the seed length, and root length was equal to or greater than seed length. 100 seeds were treated in each treatment. The experiment was repeated three times.

The results showed that the germination rates of the wheat seeds of the contrast (i.e. the germination rates of the wheat seeds treated with clear water). VdAL of 1000 times dilution, VdAL of 2000 times dilution, VdAL of 5000 times dilution, and VdAL of 10000 times dilution were 95.31±1%, 83.26±1%, 92.51±1%, 97.67±1% and 99.5011% respectively. After the wheat seeds were treated with the 1000 times diluted VdAL, the 2000 times diluted VdAL, the 5000 times diluted VdA and the 10000 times diluted VdAL, the germination rates were improved by −12.64%, −0.03%, 2.48% and 4.40% respectively. It indicated that the agent of VdAL with proper concentration can promote germination of wheat seeds.

Experiment II

The seeds of the variety of wheat, Zhongmai 816, were respectively soaked into a 5000 times diluted VdAL and a 10000 times diluted VdAL of Example 1 and clear water for 24 hours, and then were sowed into soil. The day of sowing was recorded as the first day. The wheat seedlings were taken out of the soil on the 3$^{rd}$ day after sowing. The fresh weight of the wheat seedlings was weighed.

The result showed that the fresh weights of individual plant of wheat treated with the 5000 times diluted VdAL, the 10000 times diluted VdAL and clear water were 0.128±0.022 g, 0.141±0.022 g, and 0.111±0.022 g respectively. After the seeds were soaked into the 5000 times diluted VdAL and the 10000 times diluted VdAL, the fresh weights of individual plant of wheat were improved by 15.32% and 27.03% respectively. The fresh weight of individual plant of wheat soaked into the 10000 times diluted VdAL was significantly higher than that of wheat soaked into clear water. It indicated that the agent of VdAL can promote vegetative growth of wheat.

2. The Agent of VdAL can Improve the Yield of Wheat

Field experiment was designed as follows. The experiment adopted randomized block design. Three replicate blocks provided. Each replicate block was randomly provided with five treatment areas, which were respectively VdAL treatment area I, VdAL treatment area II, VdAL treatment area III, VdAL treatment area IV and contrast treatment area. The area of each treatment area was 0.5 mu.

Wheat was treated once at the flowering stage of the seeds of the variety, Zhongmai 816, in VdAL treatment area I according to the following method. VdAL of 2500 times dilution of Example 1 with 45-50 kg per mu was sprayed to wheat leaves by the means of top spraying (mechanical spraying) to obtain wheat treated with a 2500 times diluted VdAL. The spraying was performed on morning or at evening, and preferably not at the high temperature period at noon. The agent of VdAL was preferably not mixed with pesticides and fertilizers at spraying. The agent of VdAL should be sprayed once again if it rained within 2 hours after being sprayed.

According to the treatment method of VdAL treatment area I, the 2500 times diluted VdAL was replaced with a 5000 times diluted VdAL to treat VdAL treatment area II. Other steps remained unchanged. Wheat treated with the 5000 times diluted VdAL was obtained.

According to the treatment method of VdAL treatment area I, the 2500 times diluted VdAL was replaced with a 10000 times diluted VdAL to treat VdAL treatment area III. Other steps remained unchanged. Wheat treated with the 10000 times diluted VdAL was obtained.

According to the treatment method of VdAL treatment area I, the 2500 times diluted VdAL was replaced with a 20000 times diluted VdAL to treat VdAL treatment area IV. Other steps remained unchanged. Wheat treated with the 20000 times diluted VdAL was obtained.

According to the treatment method of VdAL treatment area I, the 2500 times diluted VdAL was replaced with clear water to treat the contrast treatment area. Other steps remained unchanged. Untreated wheat was obtained.

The yields of wheat in each treatment were statistically analyzed. The results showed that the yield of wheat treated with the 2500 times diluted VdAL was 8679 kg/ha, not improved; the average yields of wheat treated with the 5000 times diluted VdAL, the 10000 times diluted VdAL, the 20000 times diluted VdAL and clear water were 8942 kg/ha, 9485 kg/ha, 9231 kg/ha and 8772 kg/ha respectively; and after the wheat was treated with the 5000 times diluted VdAL, the 10000 times diluted VdAL, the 20000 times diluted VdAL, the yields were improved by 1.94%, 8.13% and 5.23% respectively.

The thousand-grain weight, the number of effective spikes, the grain number per spike and the length of spike of wheat were statistically analyzed. The results were shown in Table 7. The result showed that, after the wheat was treated with the 5000 times diluted VdAL, the number of effective spikes was increased by 1.5%, and the grain number per spike was increased by 0.5%; after the wheat was treated with the 10000 times diluted VdAL, the number of effective spikes was increased by 7%, and the grain number per spike was increased by 3.5%; and after the wheat was treated with the 20000 times diluted VdAL, the number of effective spikes was increased by 2.3%, and the grain number per spike was increased by 3.7%.

TABLE 7 the means of the thousand-grain weight, the number of effective spikes, the grain number per spike and the length of spike of wheat in different treatment

| Treatment | Thousand-grain weight: Thousand-grain weight (g) | Thousand-grain weight: Increasing rate (%) | Number of effective spikes: Number of effective spikes(spikes/ha) | Number of effective spikes: Increasing rate (%) | Grain number per spike: Grain number per spike (grains/pike) | Grain number per spike: Increasing rate (%) | Length of spike: Length of spike (cm) | Length of spike: Increasing rate (%) |
|---|---|---|---|---|---|---|---|---|
| CK | 37.69 | / | 1293.33 | / | 30.96 | / | 8.56 | / |
| Treatment 1 | 37.5 | −0.5 | 1322.67 | 2.3 | 32.12 | 3.7 | 8.53 | −0.3 |
| Treatment 2 | 36.86 | −2.2 | 1384.33 | 7 | 32.05 | 3.5 | 8.65 | 1 |

TABLE 7-continued the means of the thousand-grain weight, the number of effective spikes,
the grain number per spike and the length of spike of wheat
in different treatment

| Treatment | Thousand-grain weight | | Number of effective spikes | | Grain number per spike | | Length of spike | |
| --- | --- | --- | --- | --- | --- | --- | --- | --- |
| | Thousand-grain weight (g) | Increasing rate (%) | Number of effective spikes(spikes/ha) | Increasing rate (%) | Grain number per spike (grains/pike) | Increasing rate (%) | Length of spike (cm) | Increasing rate (%) |
| Treatment 3 | 37.68 | 0 | 1313 | 1.5 | 31.13 | 0.5 | 8.58 | 0.2 |
| Treatment 4 | 37.6 | −0.1 | 1289.33 | −0.4 | 30.74 | −0.7 | 8.78 | 2.6 |

Note:
Treatment 1 represented the treatment with the 20000 times diluted VdAL, Treatment 2 represented the treatment with the 10000 times diluted VdAL, Treatment 3 represented the treatment with the 5000 times diluted VdAL, Treatment 4 represented the treatment with the 2500 times diluted VdAL, and CK represented untreatment (i.e., the treatment with clear water).

Example 5 the Agent of VdAL can Increase the Fruit Number of Individual Plant of Tomato Field experiment was designed as follows. The experiment adopted randomized block design. Three replicate blocks were provided. Each replicate block was randomly provided with three treatment areas, which were respectively VdAL treatment area I, VdAL treatment area II and contrast treatment area. The area of each treatment area was 0.1 mu.

The VdAL was respectively sprayed to the variety of tomato, Fux, at early flowering stage and on the 15th day after the first treatment in VdAL treatment area I according to the following method. A 1000 times diluted VdAL of Example 1 with 45-50 kg per mu was sprayed to tomato leaves by the means of top spraying (mechanical spraying) to obtain tomato treated with the 1000 times diluted VdAL. The day of first spraying was recorded as 0 day after spraying. The spraying was performed on morning or at evening, and preferably not at the high temperature period at noon. The agent of VdAL was preferably not mixed with pesticides and fertilizers at spraying. The agent of VdAL should be sprayed once again if it rained within 2 hours after being sprayed.

According to the treatment method of VdAL treatment area I, the 1000 times diluted VdAL was replaced with a 3000 times diluted VdAL to treat VdAL treatment area II. Other steps remained unchanged. Tomatoes treated with the 3000 times diluted VdAL were obtained.

According to the treatment method of VdAL treatment area I, the 1000 times diluted VdAL was replaced with clear water to treat the contrast treatment area. Other steps remained unchanged. Untreated tomatoes were obtained.

The fruit number of individual plant of tomato was statistically analyzed on the 20th day after spraying. The result showed that the average fruit number of individual plant of tomato treated with VdAL of 1000 times dilution, VdAL of 3000 times dilution and clearwater were 34.9, 40.4 and 33.3 respectively, and the fruit number of individual plant of tomato treated with VdAL of 1000 times dilution and VdAL of 3000 times dilution were improved by 4.8% and 21.3% respectively. This indicated that the agent of VdAL could promote tomato fruit.

Example 6 the Agent of VdAL can Promote the Growth of Green-Stem Cabbage

Field experiment was designed as follows. The experiment adopted randomized block design. Three replicate blocks were provided. Each replicate block was randomly provided with five treatment areas, which were respectively VdAL treatment area I, VdAL treatment area II, VdAL treatment area III, VdAL treatment area IV and contrast treatment area. The area of each treatment area was 0.2 mu.

The VdAL was sprayed once to the variety of green-stem cabbage, Huali, in VdAL treatment area I at two-leaf one-tip stage according to the following method. A 2000 times diluted VdAL of Example 1 with 45-50 kg per mu was sprayed to green-stem cabbage leaves by the means of top spraying (manual spraying) to obtain green-stem cabbage treated with the 2000 times diluted VdAL. The day of spraying the VdAL was recorded as 0 day of treatment. The spraying was performed on morning or at evening, and preferably not at the high temperature period at noon. The agent of VdAL was preferably not mixed with pesticides and fertilizers at spraying. The agent of VdAL should be sprayed once again if it rained within 2 hours after being sprayed.

According to the treatment method of VdAL treatment area I, the 2000 times diluted VdAL was replaced with a 2500 times diluted VdAL to treat VdAL treatment area II. Other steps remained unchanged. Green-stem cabbages treated with the 2500 times diluted VdAL were obtained.

According to the treatment method of VdAL treatment area I, the 2000 times diluted VdAL was replaced with a 3000 times diluted VdAL to treat VdAL treatment area III. Other steps remained unchanged. Green-stem cabbages treated with the 3000 times diluted VdAL were obtained.

According to the treatment method of VdAL treatment area I, the 2000 times diluted VdAL was replaced with a 4000 times diluted VdAL to treat VdAL treatment area IV. Other steps remained unchanged. Green-stem cabbages treated with the 4000 times diluted VdAL were obtained.

According to the treatment method in VdAL, treatment area I, the 2000 times diluted VdAL was replaced with clear water to treat the contrast treatment area. Other steps remained unchanged. Untreated green-stem cabbages were obtained.

The fresh weights of 50 green-stem cabbages in different treatments were statistically analyzed on the 20th day after the treatment. The result showed that the average fresh weights of 50 green-stem cabbages treated with the 2000 times diluted VdAL, the 2500 times diluted VdAL, the 3000 times diluted VdAL, the 4000 times diluted VdAL and clear water were 2.960 kg, 3.270 kg, 3.835 kg, 3.895 kg and 1.912 kg respectively; and the fresh weights of 50 green-stem cabbages treated with the 2000 times diluted VdAL, the 2500 times diluted VdAL, the 3000 times diluted VdAL, and the 4000 times diluted VdAL were improved by 54.8%, 71.0%, 100.6% and 103.7% respectively. This indicated that the agent of VdAL could promote the growth of green-stem cabbage.

Example 7 Effects of the Agent of VdAL in Other Crops

1. The Agent of VdAL can Promote the Growth of Cucumber, Improve the Yield and Delay Aging Thereof Field experiment was designed as follows. The experiment adopted randomized block design. Three replicate blocks were provided. Each replicate block was randomly provided with five treatment areas, which were respectively VdAL treatment area I, VdAL treatment area II, VdAL treatment area III, VdAL treatment area IV and contrast treatment area. The area of each treatment area was 0.1 mu.

The VdAL was sprayed to the variety of cucumber, Jinza No. 1 in VdAL treatment area I at early flowering stage and on the $15^{th}$ day after the first treatment respectively according to the following method. A 300 times diluted VdAL of Example 1 with 45-50 kg per mu was sprayed to cucumber leaves by the means of top spraying (manual spraying) to obtain cucumber treated with the 300 times diluted VdAL. The day of the first time of spraying VdAL was recorded as 0 day after spraying. The spraying was performed on morning or at evening, and preferably not at the high temperature period at noon. The agent of VdAL was preferably not mixed with pesticides and fertilizers at spraying. The agent of VdAL should be sprayed once again if it rained within 2 hours after being sprayed.

According to the treatment method of VdAL treatment area I, the 300 times diluted VdAL of was replaced with a 600 times diluted VdAL to treat VdAL treatment area II. Other steps remained unchanged. Cucumbers treated with the 600 times diluted VdAL were obtained.

According to the treatment method of VdAL treatment area I, the 300 times diluted VdAL of was replaced with a 900 times diluted VdAL to treat VdAL treatment area III. Other steps remained unchanged. Cucumbers treated with the 900 times diluted VdAL were obtained.

According to the treatment method of VdAL treatment area I, the 300 times diluted VdAL of was replaced with a 2000 times diluted VdAL to treat VdAL treatment area IV. Other steps remained unchanged. Cucumbers treated with the 2000 times diluted VdAL were obtained.

According to the treatment method of VdAL treatment area I, the 300 times diluted VdAL was replaced with clear water to treat the contrast treatment area. Other steps remained unchanged. Untreated cucumbers were obtained.

The result of cucumber was statistically analyzed on the $20^{th}$ day after spraying. The result showed that the agent of VdAL could improve the fruit setting rate of cucumber, promote the expansion of cucumber and improve the yield of cucumber (FIG. 3), which indicated that the agent of VdAL could promote vegetative growth and reproductive growth of cucumber. Growth vigor of cucumber was observed on the $20^{th}$ day after spraying. The result showed that the growth vigor of cucumber treated with the agent of VdAL was better than that of untreated cucumber (FIG. 4), which indicated that the agent of VdAL could promote vegetative growth of cucumber. The situation of cucumber aging was observed on the $45^{th}$ day after spraying. The result showed that the aging situation of untreated cucumber was more serious than that of cucumber treated with the agent of VdAL (FIG. 5), which indicated that VdAL could delay aging of cucumber.

2. The Agent of VdAL can Improve the Fruit Setting Rate and Yield of Cherry Tomato Field experiment was designed as follows. The experiment adopted randomized block design. Three replicate blocks were provided. Each replicate block was randomly provided with two treatment areas, which were respectively VdAL treatment area and contrast treatment area. The area of each treatment area was 1 mu.

The VdAL was sprayed once to the variety of cherry tomato, Jingdan No. 2, at flowering stage in VdAL treatment area according to the following method. A 2000 times diluted VdAL of Example 1 with 45-50 kg per mu was sprayed to cherry tomato leaves by the means of top spraying (manual spraying) to obtain cherry tomato treated with the 2000 times diluted VdAL. The day of spraying the agent of VdAL was recorded as 0 day of the treatment. The spraying was performed on morning or at evening, and preferably not at the high temperature period at noon. The agent of VdAL was preferably not mixed with pesticides and fertilizers at spraying. The agent of VdAL should be sprayed once again if it rained within 2 hours after being sprayed.

According to the treatment method of VdAL treatment area, the 2000 times diluted VdAL was replaced with clear water to treat the contrast treatment area. Other steps remained unchanged. Untreated cherry tomatoes were obtained.

The result of cherry tomato was observed on the 7-$10^{th}$ day after treatment. The result showed that the agent of VdAL could improve the fruit setting rate and yield of cherry tomato (FIG. 6), which indicated that the agent of VdAL could promote the growth of cherry tomato.

3. The Agent of VdAL can Promote the Growth of Strawberry

Field experiment was designed as follows. The variety of strawberry was Fengxiang. The experiment adopted randomized block design. Three replicate blocks were provided. Each replicate block was randomly provided with two treatment areas, which were respectively VdAL treatment area and contrast treatment area. The area of each treatment area was 1 mu.

The VdAL was sprayed once to the variety of strawberry, Fengxiang, at flowering stage in VdAL treatment area according to the following method. A 2000 times diluted VdAL of Example 1 with 45-50 kg per mu was sprayed to strawberry leaves by the means of top spraying (manual spraying) to obtain strawberry treated with the 2000 times diluted VdAL. The day of spraying the agent of VdAL was recorded as 0 day of the treatment. The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area, the 2000 times diluted VdAL was replaced with clear water to treat the contrast treatment area. Other steps remained unchanged. Untreated strawberries were obtained.

The growth situation of strawberry was observed on the 7-$10^{th}$ day after treatment. The result showed that the agent of VdAL could promote vegetative growth of strawberry (FIG. 7).

4. The Agent of VdAL can Promote the Growth of Melon

Field experiment was designed as follows. The variety of melon was Super Cuibaoxiang. The experiment adopted randomized block design. Three replicate blocks were provided. Each replicate block was randomly provided with two treatment areas, which were respectively VdAL treatment area and contrast treatment area. The area of each treatment area was 1 mu.

The VdAL was sprayed once to the variety of melon, Super Cuibaoxiang, at seedling stage in VdAL treatment area according to the following method. A 2000 times diluted VdAL of Example 1 with 45-50 kg per mu was sprayed to melon leaves by the means of top spraying (manual spraying) to obtain melon treated with the 2000 times diluted VdAL. The day of spraying the agent of VdAL was recorded as 0 day of the treatment. The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area, the 2000 times diluted VdAL was replaced with clear water to treat the contrast treatment area. Other steps remained unchanged. Untreated melons were obtained.

Figure 8:
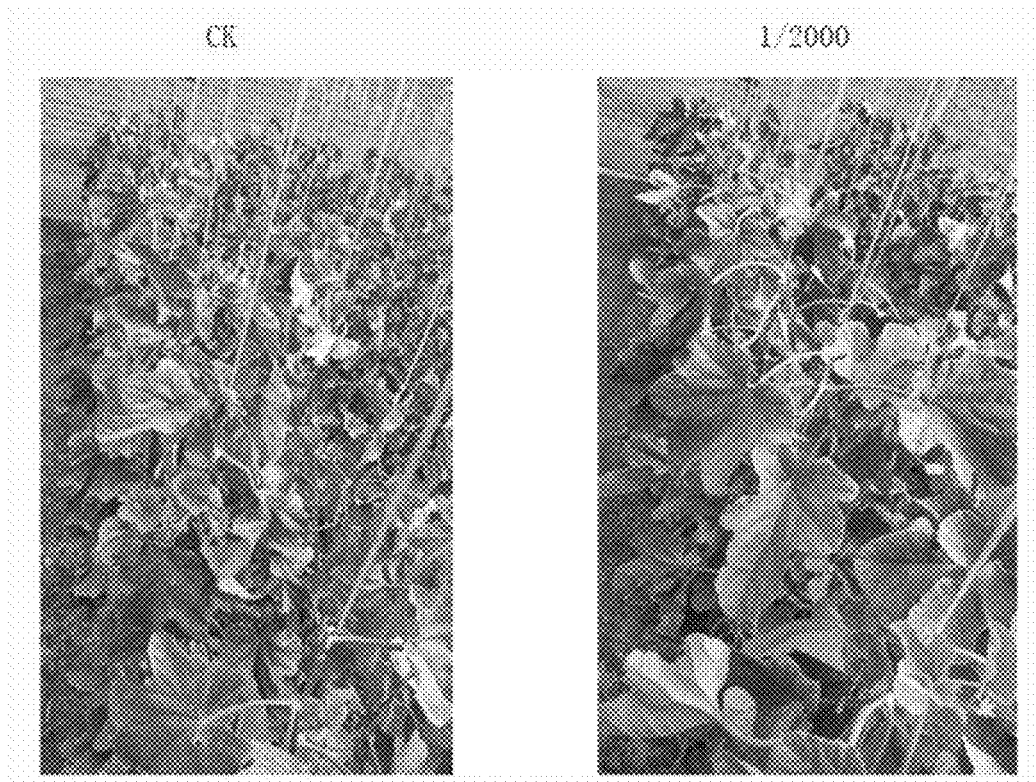
FIG. 8 shows melon with different treatments, wherein CK represents untreated muskmelon, and 1/2000 represents muskmelon treated with 2000 times diluted VdAL.

The growth situation of melon was observed on the $30^{th}$ day after treatment. The result showed that VdAL could promote vegetative growth of melon (FIG. 8).

5. The Agent of VdAL can Promote the Growth of Sweet Pepper

Field experiment was designed as follows. The experiment adopted randomized block design. Three replicate blocks were provided. Each replicate block was randomly provided with two treatment areas, which were respectively VdAL treatment area and contrast treatment area. The area of each treatment area was 1 mu.

The VdAL was sprayed once to the variety of sweet pepper, Ruiyou 816, at flowering stage in VdAL treatment area according to the following method. A 1000 times diluted VdAL of Example 1 with 45-50 kg per mu was sprayed to sweet pepper leaves by the means of top spraying (manual spraying) to obtain sweet pepper treated with the 1000 times diluted VdAL. The day of spraying the agent of VdAL was recorded as 0 day of the treatment. The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area, the 1000 times diluted VdAL was replaced with clear water to treat the contrast treatment area. Other steps remained unchanged. Untreated sweet peppers were obtained.

Figure 9:
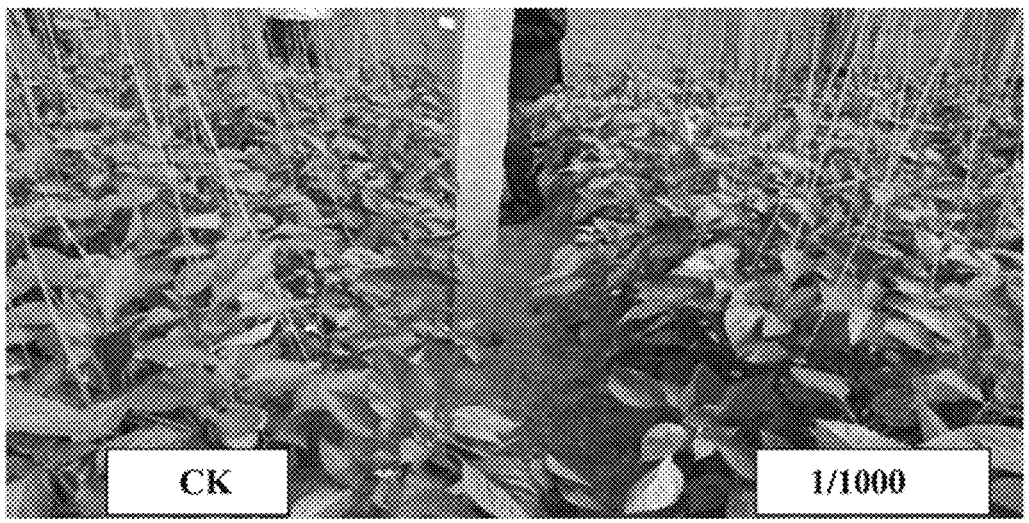
FIG. 9 shows sweet pepper with different treatments, wherein CK represents untreated sweet pepper, and 1/1000 represents sweet pepper treated with 1000 times diluted VdAL.

The growth situation of sweet pepper was observed on the $7$-$10^{th}$ day after treatment. The result showed that the sweet pepper was vigorous in growth and its leaves were dark green after the agent of VdAL was sprayed (FIG. 9), which indicated that the agent of VdAL could promote vegetative growth of sweet pepper.

6. The Agent of VdAL can Promote Seedling Emergence and Growth of Soybean

The seeds of the variety of soybean, King of China soybean, were soaked into a 1000 times diluted VdAL, a 3000 times diluted VdAL, a 5000 times diluted VdAL, a 10000 times diluted VdAL and a 20000 times diluted VdAL of Example 1 and clear water, respectively, for 24 hours, and then accelerate germination for 72 hours at 25° C. in trays, in which two layers of sterile filter paper wetted with sterile water were spread. The germination rate of the soybean seeds was statistically analyzed. 100 seeds were treated in each treatment. The experiment was repeated three times.

The result showed (FIG. 10) that the germination rates of soybean seed treated with the 3000 times diluted VdAL and the 5000 times diluted VdAL were improved respectively, which indicated that the agent of VdAL could promote germination of soybean seed.

Experiment II

The seeds of the variety of soybean, King of China soybean, were soaked into a 5000 times diluted VdAL, of Example 1 and clear water, respectively, for 24 hours, and then were sowed into soil. The day of sowing was recorded as the first day after sowing. Soybean seedlings were taken out of the soil on the $20^{th}$ day after sowing. The fresh weight of the soybean seedlings was weighed (FIG. 11).

The result showed that the fresh weights of individual plant of soybean treated with the 5000 times diluted VdAL and clear water were 1.59±0.3 g and 1.36±0.3 g respectively; after the seeds were soaked into the 5000 times diluted VdAL, the fresh weight of individual plant of soybean was improved by 16.91%; the fresh weights of the ground part of individual plant of soybean treated with the 5000 times diluted VdAL and clear water were 1.36±0.3 g and 1.06±0.3 g respectively; and after the seeds were soaked into the 5000 times diluted VdAL, the fresh weight of the ground part of individual plant of soybean was improved by 28.30%, which was significantly higher than the fresh weight of the ground part of individual plant of soybean treated with clear water. This indicated that the agent of VdAL could promote vegetative growth of soybean.

Example 8 the Agent of VdAL can Promote the Growth of Rice and Improve the Yield Thereof Field experiment was designed as follows. The experiment adopted randomized block design. Three replicate blocks were provided. Each replicate block was randomly provided with four treatment areas, which were respectively VdAL treatment area I, VdAL treatment area II, VdAL treatment area III and contrast treatment area. The area of each treatment area was 0.1 mu.

The variety of rice, Nongda 502, of VdAL treatment area I was treated once at flowering stage according to the following method. A 10000 times diluted VdAL of Example 1 with 45-50 kg per mu was sprayed to rice leaves by the means of top spraying (manual spraying) to obtain rice treated with the 10000 times diluted VdAL (1/10000). The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area I, the 10000 times diluted VdAL was replaced with a 20000 times diluted VdAL to treat VdAL treatment area II. Other steps remained unchanged. Rice treated with the 20000 times diluted VdAL (1/20000) was obtained.

According to the treatment method of VdAL treatment area I, the 10000 times diluted VdAL was replaced with a 40000 times diluted VdAL to treat VdAL treatment area III. Other steps remained unchanged. Rice treated with the 40000 times diluted VdAL (1/40000) was obtained.

According to the treatment method of VdAL treatment area I, the 10000 times diluted VdAL was replaced with clear water to treat the contrast treatment area. Other steps remained unchanged. Untreated rice (CK) was obtained.

The yields of rice in each treatment were statistically analyzed. The result (FIG. 12) showed that the average yields of rice treated with the 10000 times diluted VdAL, the 20000 times diluted VdAL, the 40000 times diluted VdAL and clear water were 447.29 kg/mu, 408.35 kg/mu, 390.14 kg/mu and 398.37 kg/mu, respectively, and the yields of rice treated with the 10000 times diluted VdAL and the 20000 times diluted VdAL were improved by 12.28% and 2.51% respectively.

Example 9 the Agent of VdAL can Improve the Drought Resistance of Wheat

The experiments were repeated three times. The specific steps of each repeated experiment were shown as follows.

Experiment I

The seeds of wheat, Zhongmai 816, were divided into four groups, i.e. group 1, group 2, group 3 and group 4. Each group had 50 seeds.

The agent of VdAL of Example 1 was added into Fuwu (Beinong (Haili) Zhuozhou Seed Coat Co., Ltd.) having a mass percentage concentration of 6% to obtain the liquid in which the mass percentage concentration of the agent of VdAL was 2%. The liquid was named 2.0%+Fuwu. Wheat seeds of group 1 were treated by 2.0%+Fuwu according to the following method. 100-200 g of 2.0%+Fuwu was blended with 1.5-2 kg of water, and was stirred uniformly, then was mixed with 100 kg of seeds, and the following was to be stirred uniformly. The seeds were dried in the shade for sowing. Then the wheat seeds of group 1 were sowed into soil. Watering wheat was stopped (i.e., water-control treatment) at the three-leaf stage of wheat.

The agent of VdAL of Example 1 was added into Fuwu having a mass percentage concentration of 6% to obtain the liquid in which the mass percentage concentration of the agent of VdAL was 1%. The liquid was named 1.0%+Fuwu. Wheat seeds of group 2 were treated by 1.0%+Fuwu according to the following method. 100-200 g of 1.0%+Fuwu was blended with 1.5-2 kg of water, and was stirred uniformly, then was mixed with 100 kg of seeds, and the following was to be stirred uniformly. The seeds were dried in the shade for sowing. Then the wheat seeds of group 2 were sowed into soil. Watering wheat was stopped (i.e., water-control treatment) at the three-leaf stage of wheat.

Wheat seeds of group 3 were treated by 1.0%+Fuwu according to the following method. 100-200 g of Fuwu (Beinong (Haili) Zhuozhou Seed Coat Co., Ltd.) having a mass percentage concentration of 6% was blended with 1.5-2 kg of water, and was stirred uniformly, then was mixed with 100 kg of seeds, and the following was to be stirred uniformly. The seeds were dried in the shade for sowing. Then the wheat seeds of group 3 were sowed into soil. Watering wheat was stopped (i.e., water-control treatment) at the three-leaf stage of wheat.

Wheat seeds of group 4 were treated with clear water as a contrast (CK) according to the following method. 100 kg of seeds were mixed with 1.5-2 kg of water, and were stirred uniformly. The seeds were dried in the shade for sowing. Then the wheat seeds of group 4 were sowed into soil. Watering wheat was stopped (i.e., water-control treatment) at the three-leaf stage of wheat.

The first day of stopping watering was recorded as $1^{st}$ day of water-control. The result showed that the agent VdAL added into a seed coating to treat wheat seeds could significantly improve drought resistance of wheat. All of the wheat of group 1 died within 20 days after water-control. All of the wheat of group 2 died within 15 days after water-control. All of the wheat of group 3 died within 10 days after water-control. All of the wheat of group 4 died within 12 days after water-control. The time when all of the wheat of group 1 died was significantly longer than the time when all of the wheat of group 3 and group 4 died, respectively. The time when all of the wheat of group 2 died was significantly longer than the time when all of the wheat of group 3 and group 4 died, respectively. The growth situation of wheat of each group on 7 days after water-control was shown in FIG. 13.

Experiment II

The seeds of wheat, Zhongmai 816, were divided into six groups, i.e. group 1, group 2, group 3, group 4, group 5 and group 6. Each group had 50 seeds.

Wheat seeds of group 1 were treated with clear water as a contrast (CK1) according to the following method. 100 kg of seeds were mixed with 1.5-2 kg of clear water, and were stirred uniformly. The seeds were dried in the shade for sowing. Then the wheat seeds of group 1 were sowed into soil. Watering wheat was stopped at three-leaf stage. The wheat was re-watered on the $7^{th}$ day after watering was stopped.

The agent of VdAL of Example 1 was added into Fuwu having a mass percentage concentration of 6% to obtain the liquid in which the mass percentage concentration of the agent of VdAL was 0.2%. The liquid was named 0.2%+Fuwu. Wheat seeds of group 2 were treated by 0.2%+Fuwu according to the following method. 100-200 g of 0.2%+Fuwu was blended with 1.5-2 kg of water, and was stirred uniformly, then was mixed with 100 kg of seeds, and the following was to be stirred uniformly. The seeds were dried in the shade for sowing. Then the wheat seeds of group 2 were sowed into soil. Watering wheat was stopped at three-leaf stage. The wheat was re-watered on the $7^{th}$ day after watering was stopped.

The VdAL of Example 1 was added into Fuwu having a mass percentage concentration of 6% to obtain the liquid in which the mass percentage concentration of the agent of VdAL was 1%. The liquid was named 1.0%+Fuwu. Wheat seeds of group 3 were treated by 1.0%+Fuwu according to the following method. 100-200 g of 1.0%+Fuwu was blended with 1.5-2 kg of water, and was stirred uniformly, then was mixed with 100 kg of seeds, and the following was to be stirred uniformly. The seeds were dried in the shade for sowing. Then the wheat seeds of group 3 were sowed into soil. Watering wheat was stopped at three-leaf stage. The wheat was re-watered on the $7^{th}$ day after watering was stopped.

The VdAL of Example 1 was added into Fuwu having a mass percentage concentration of 6% to obtain the liquid in which the mass percentage concentration of the agent of VdAL was 2%. The liquid was named 2.0%+Fuwu. Wheat seeds of group 4 were treated by 2.0%+Fuwu according to the following method. 100-200 g of 2.0%+Fuwu was blended with 1.5-2 kg of water, and was stirred uniformly, then was mixed with 100 kg of seeds, and the following was to be stirred uniformly. The seeds were dried in the shade for sowing. Then the wheat seeds of group 4 were sowed into soil. Watering wheat was stopped at three-leaf stage. The wheat was re-watered on the $7^{th}$ day after watering was stopped.

The VdAL of Example 1 was added into Fuwu having a mass percentage concentration of 6% to obtain the liquid in which the mass percentage concentration of the agent of VdAL was 4%. The liquid was named 4.0%+Fuwu. Wheat seeds of group 5 were treated by 4.0%+Fuwu according to the following method. 100-200 g of 4.0%+Fuwu was blended with 1.5-2 kg of water, and was stirred uniformly, then was mixed with 100 kg of seeds, and the following was to be stirred uniformly. The seeds were dried in the shade for sowing. Then the wheat seeds of group 5 were sowed into soil. Watering wheat was stopped at three-leaf stage. The wheat was re-watered on the $7^{th}$ day after watering was stopped.

Wheat seeds of group 6 were treated by 6% Fuwu as a contrast (CK2) according to the following method. 100-200 g of Fuwu (Beinong (Haili) Zhuozhou Seed Coat Co., Ltd.) having a mass percentage concentration of 6% was blended with 1.5-2 kg of water, and was stirred uniformly, then was mixed with 100 kg of seeds, and the following was to be stirred uniformly. The seeds were dried in the shade for sowing. Then the wheat seeds of group 6 were sowed into soil. Watering wheat was stopped at three-leaf stage. The wheat was re-watered on the $7^{th}$ day after watering was stopped.

The chlorophyll content of wheat leaves of each group was determined by SPAD-502Plus (Beijing Bolun Jingwei Science and Technology Development Co., Ltd.) on the same day that watering for each group was stopped. The result was shown in FIG. 14, in which 1 represented group 1, 2 represented group 2, 3 represented group 3, 4 represented group 4, 5 represented group 5, 6 represented group 6, and the unit of longitudinal coordinates was SPAD. The average chlorophyll contents of wheat of group 1, group 2, group 3, group 4, group 5 and group 6 were 34.1 SPAD, 34.5 SPAD, 34.5 SPAD, 34.4 SPAD, 33.6 SPAD and 33.9 SPAD respectively. The chlorophyll contents of wheat of group 2, group 3 and group 4 were significantly higher than those of group 1 and group 6 respectively, and the chlorophyll content of group 5 was lower than those of group 1 and group 6, which indicated that the agent of VdAL with a proper concentration could improve the chlorophyll content of wheat.

The re-watering index was calculated on the $4^{th}$ day after re-watering treatment for each group, wherein the re-watering index=(1×I-level plant number+2×II-level plant number+3×III-level plant number+4×IV-level plant number)/(4× investigated plant number).

The grading standards of plant were as follows:

Level 0: after watering was recovered, the curling area of individual leaf was 100%, and leaf did not become green;

Level I: after watering was recovered, the curling area of individual leaf was 100%, and leaf started to become green;

Level II: after watering was recovered, the curling area of individual leaf was more than or equal to 50% and less than 100%;

Level III: after watering was recovered, the curling area of individual leaf was more than or equal to 0% and less than 50%;

Level IV: after watering was recovered, the curling area of individual leaf was 0%.

The result was as shown FIG. 15, in which 1 represented group 1, 2 represented group 2, 3 represented group 3, 4 represented group 4, 5 represented group 5, 6 represented group 6. The average re-watering indexes of wheat of group 1 (CK1), group 2, group 3, group 4, group 5 and group 6 (CK2) were 0.348, 0.516, 0.523, 0.43, 0.219 and 0.323 respectively. The re-watering indexes of wheat of group 2, group 3 and group 4 were significantly higher than those of group 1 and group 6, and the re-watering index of group 5 was lower than those of group 1 and group 6, which indicated that the agent of VdAL with a proper concentration could improve the drought resistance of wheat.

Example 10 the Agent of VdAL can Improve the Quality of Grape

Field experiment was designed as follows. The place for experiment was Dunhuang, Gansu province. The experiment adopted randomized block design. Three replicate blocks were provided. Each replicate block was randomly provided with two treatment areas, which were respectively VdAL treatment area and contrast treatment area. The area of each treatment area was 0.1 mu.

The variety of grape red globe (Gansu Yongdeng Yongsheng Red Grape Professional Cooperative) was treated once at flowering stage in VdAL treatment area according to the following method. A 3000 times diluted VdAL of Example 1 with 45-50 kg per mu was sprayed to grape leaves by the means of top spraying (manual spraying) to obtain grape treated with the 3000 times diluted VdAL (1/3000). The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area, the 3000 times diluted VdAL was replaced with clear water to treat the contrast treatment area. Other steps remained unchanged. Untreated grapes were obtained (contrast, CK).

The mature time of grape in each treatment was statistically analyzed. The result showed that the average mature times of grape treated with the 3000 times diluted VdAL and clear water were September 15 (85 days after flowering stage, or 75 days after VdAL treatment) and September 20 (90 days after flowering stage, or 80 days after clear water treatment), respectively. The mature time of grape treated with the 3000 times diluted VdAL was 5 days early.

The Vc content of the mature grape was determined according to a 2,6-dichlorophenol indophenol titration method. The result showed that the average Vc contents of grape treated with the 3000 times diluted VdAL and clear water were respectively 18.20 mg/100 g fresh weight and 12.10 mg/100 g fresh weight. The Vc content of the grape treated with the 3000 times diluted VdAL was improved by 50.4%.

By observing mature grape, it showed that the color of grape sprayed VdAL was brighter and the bunch of grape was compact and the fruit dropped down uneasily (FIG. 16).

Example 11 the Agent of VdAL can Promote the Maturity and Coloration of Cherry and Improve the Yield of Cherry Field experiment was designed as follows. The place of experiment was Fusban District, Yantai City. The experiment adopted randomized block design. Three replicate blocks were provided. Each replicate block was randomly provided with two treatment areas, which were respectively VdAL treatment area and contrast treatment area. The area of each treatment area was 0.1 mu.

The variety of cherry, Longguan (Yantai Qixia Qunli Fruits and Nursery Stock Professional Cooperatives), was treated once at flowering stage in VdAL treatment area according to the following method. A 5000 times diluted VdAL of Example 1 with 45-50 kg per mu was sprayed to cherry leaves by the means of top spraying (manual spraying) to obtain cherries treated with the 5000 times diluted VdAL (1/5000). The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area, the 5000 times diluted VdAL was replaced with clear water to treat the contrast treatment area. Other steps remained unchanged. Untreated cherries were obtained (contrast, CK).

The mature time of cherry in each treatment was statistically analyzed. The result showed that the average mature time of cherry treated with the 5000 times diluted VdAL and clear water was respectively May 1 (52 days after flowering stage and VdAL treatment) and May 6 (57 days after VdAL treatment). The mature time of cherry treated with the 5000 times diluted VdAL was 5 days early.

The yield of cherry in each treatment was statistically analyzed. The result showed that the average yields of cherry treated with the 5000 times diluted VdAL and clear water were 2200 kg and 1715 kg respectively. The yield of cherry treated with the 5000 times diluted VdAL was improved by 28.28%.

When cherry was mature (52 days after VdAL treatment, or 57 days after clear water treatment), the appearance of cherry was observed. The result showed that the color of the cherry treated with VdAL was significantly redder than that of untreated cherry (FIG. 17), which indicated that VdAL could promote coloration of cherry.

Example 12 the Agent of VdAL can Promote the Growth of Can-Like Radish and Improve the Palatability Thereof Field experiment was designed as follows. The experiment adopted randomized block design. Three replicate blocks were provided. Each replicate block was randomly provided with two treatment areas, which were respectively VdAL treatment area and contrast treatment area. The area of each treatment area was 0.1 mu.

The variety of can-like radish, 791 (Zhengzhou Sanhe Agricultural Science and Technology Development Co., Ltd.), was treated once at root expansion stage in VdAL treatment area according to the following method. A 5000 times diluted VdAL of Example 1 with 45-50 kg per mu was sprayed to can-like radish leaves by the means of top spraying (manual spraying) to obtain can-like radish treated with the 5000 times diluted VdAL (1/5000). The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area, the 5000 times diluted VdAL was replaced with clear water to treat the contrast treatment area. Other steps remained unchanged. Untreated can-like radishes were obtained (contrast, CK).

The yield of can-like radish in each treatment was statistically analyzed on the $20^{th}$ day after VdAL/clear water treatment (FIG. 18). The result showed that the average weights of individual root tuber of can-like radish treated with the 5000 times diluted VdAL and clear water were 0.90 kg and 0.85 kg respectively. The average weight of individual root tuber of the can-like radish treated with the 5000 times diluted VdAL was improved by 5.88%. The average fresh weights of individual plant of can-like radish treated with the 5000 times diluted VdAL and clear water were 1.20 kg and 1.09 kg respectively. The average fresh weight of individual plant of can-like radish treated with the 5000 times diluted VdAL was improved by 10.09%.

30 experienced evaluators were selected to evaluate the brittleness of the can-like radish treated with the above two methods (FIG. 18). Apple red Fuji with a score of 10 for the brittleness was used as a reference sample. 10 parts of samples of each kind of can-like radish were selected for 10 parallel experiments. The mean of scores was calculated. The result showed that the average score of the brittleness of untreated can-like radish was 5.32, and the average of brittleness score of the can-like radish treated with the 5000 times diluted VdAL was 6.55. The average relative deviations of 10 parallel experiments were less than 20% after determination, respectively, which meet the experimental requirement. The average score of the brittleness of untreated can-like radish was significantly less than that of the can-like radish treated with the 5000 times diluted VdAL.

Other 30 experienced evaluators were selected to evaluate the sweetness of the can-like radish treated with the above two method. Apple red Fuji with a score of 10 for the brittleness was used as a reference sample. 10 parts of samples of each kind of can-like radish were selected for 10 parallel experiments. The mean of scores was calculated. The result showed that the average score of the sweetness of untreated can-like radish was 4.27, and the average score of the sweetness of can-like radish treated with the 5000 times diluted VdAL was 5.56. The average relative deviations of 10 parallel experiments were less than 20% after determination, respectively, which meet the experimental requirement. The average score of the sweetness of untreated can-like radish was significantly less than that of the can-like radish treated with the 5000 times diluted VdAL.

This indicated that the agent of VdAL could improve the brittleness and sweetness of can-like radish and the can-like radish treated with the agent of VdAL had strong palatability.

Example 13 the Agent of VdAL can Promote the Growth of Spinach and Improve the Yield Thereof Field experiment was designed as follows. The experiment adopted randomized block design. Three replicate blocks were provided. Each replicate block was randomly provided with three treatment areas, which were respectively VdAL treatment area I, VdAL treatment area II and contrast treatment area. The area of each treatment area was 0.1 mu.

The variety of spinach, Qiulv (Zhengzhou Sanhe Agricultural Science and Technology Development Co., Ltd.), was treated once at three-leaf stage in VdAL treatment area I according to the following method. A 4000 times diluted VdAL of Example 1 with 15-20 kg per mu was sprayed to spinach leaves by the means of top spraying (manual spraying) to obtain spinach treated with the 4000 times diluted VdAL (1/4000). The spraying was performed on morning or at evening, and preferably not at the high temperature period at noon. The agent of VdAL was prohibited to be mixed with pesticides and fertilizers at spraying. The agent of VdAL should be sprayed once again if it rained within 2 hours after being sprayed.

According to the treatment method of VdAL treatment area I, the 4000 times diluted VdAL was replaced with a 6000 times diluted VdAL to treat VdAL treatment area II. Other steps remained unchanged. Spinaches treated with the 6000 times diluted VdAL (1/6000) were obtained.

According to the treatment method of VdAL treatment area I, the 4000 times diluted VdAL was replaced with clear water to treat the contrast treatment area. Other steps remained unchanged. Untreated spinaches (CK) were obtained.

The yield of spinach in each treatment was statistically analyzed on the $20^{th}$ days after VdAL/clear water treatment. The result showed that the average yields of the spinach treated with the 4000 times diluted VdAL, the 6000 times diluted VdAL and clear water were 0.58 g/0.12 $m^2$, 0.98 kg/0.12 $m^2$ and 0.63 kg/0.12 $m^2$ respectively, and the yields of the spinach treated with the 4000 times diluted VdAL and the 6000 times diluted VdAL were improved by −7.45% and 56.38% respectively, which indicated that VdAL with a proper concentration for treating spinach could improve the yield thereof.

INDUSTRIAL APPLICATION

Experiments prove that the biological agent of VdAL according to the present invention, wherein VdAL is an active ingredient, can promote the seed germination, plant growth and fruit growth of multiple plant, improve the fruit setting number of multiple plant, and delay aging of multiple plant.

1. The average germination rate of cotton after cotton seeds are treated with the 7500 times diluted VdAL is 1.08 times that of cotton after cotton seeds are treated with clear water. When Lu No. 30 is treated with the 3000 times diluted VdAL, the cotton yield before first frost is improved by 19.48% and the total yield is improved by 17.04%. When the cotton was treated with the 5000 times diluted VdAL, the cotton yield of Lu No. 30 before first frost is improved by 21.25% and the total yield thereof is improved by 20.00%, the cotton yield of 616 before first frost is improved by 19.06% and the total yield thereof is improved by 19.69%, and the cotton yield of Lu No. 25 before first frost is improved by 16.37% and the total yield thereof is improved by 17.60%. When the cotton was treated with the 3000 times diluted VdAL, the number of boll setting of individual plant, total number of the boll per mu, ginning outturn and the yield per mu were increased by 4.5%, 1.98%, 0.24% and 1.76% respectively. When the cotton was treated with the 5000 times diluted VdAL, the number of boll setting of individual plant, total number of the boll per mu, the weight of single boll, ginning outturn and the yield per mu were increased by 3.41%, 4.41%, 1.9%, 0.49% and 5.22%, respectively.

2. After watermelon is treated with the 2000 times diluted VdLA, the fruit number of individual plant of watermelon is improved by 18.2%, and the yield is improved by 33.4%.

3. After wheat seeds are treated with the 1000 times diluted VdAL, the 2000 times diluted VdAL, the 5000 times diluted VdAL and the 10000 times diluted VdAL, the germination rates are improved by 2 times, 9 times, 12 times and 11 times, respectively. The germination rates of the wheat seeds treated with the 5000 times diluted VdAL and the 10000 times diluted VdAL are improved by 2.48% and 4.40% respectively. After seeds are soaked into the 5000 times diluted VdAL and the 10000 times diluted VdAL, the fresh weights of individual plant of wheat were improved by 15.32% and 27.03%, respectively. After wheat is treated with the 5000 times diluted VdAL, the 10000 times diluted VdAL and the 20000 times diluted VdAL, the yields are improved by 1.94%, 8.13% and 5.23%, respectively. After wheat is treated with the 5000 times diluted VdAL, the number of effective spike is increased by 1.5%, and the grain number per spike is increased by 0.5%; after the wheat is treated with the 10000 times diluted VdAL, the number of effective spike is increased by 7%, and the grain number per spike is increased by 3.5%; and after the wheat is treated with the 20000 times diluted VdAL, the number of effective spike is increased by 2.3%, and the grain number per spike is increased by 3.7%.

4. After tomatoes are treated with the 1000 times diluted VdAL and the 3000 times diluted VdAL, the fruit numbers of individual plant of tomato is improved by 4.8% and 21.3%, respectively.

5. After green-stem cabbage is treated with the 2000 times diluted VdAL, the 2500 times diluted VdAL, the 3000 times diluted VdAL and the 4000 times diluted VdAL, the fresh weights of 50 plant of green-stem cabbages are improved by 54.8%, 71.0%, 100.6% and 103.7%, respectively.

6. The VdAL can further improve the fruit setting rate of cucumber, promote the expansion of cucumber, improve the yield of cucumber, promote the growth of cucumber plant and delay aging of cucumber plant. The VdAL can further improve the fruit setting rate of cherry tomato, promote plant growth of strawberry, melon and sweet pepper, and promote germination and growth of soybean. After seeds are soaked into the 5000 times diluted VdAL, the fresh weight of individual plant of soybean is improved by 16.91%, and the ground part fresh weight of individual plant of soybean is improved by 28.30%.

7. After rice is treated with the 10000 times diluted VdAL and the 20000 times diluted VdAL, the yields are improved by 12.28% and 2.51%, respectively.

8. The average weights of individual root tuber of can-like radish treated with the 5000 times diluted VdAL and clear water are 0.90 kg and 0.85 kg, respectively. The average weight of individual root tuber of the can-like radish treated with the 5000 times diluted VdAL is improved by 5.88%. The average fresh weights of individual plant of can-like radish treated with the 5000-times diluted VdAL and clear water are 1.20 kg and 1.09 kg, respectively. The average fresh weight of individual plant of can-like radish treated with the 5000 times diluted VdAL is improved by 10.09%.

9. The average yields of spinach treated with the 4000 times diluted VdAL, the 6000 times diluted VdAL and clear water are 0.58 kg/0.12 $m^2$, 0.98 kg/0.12 $m^2$ and 0.63 kg/0.12 $m^2$ respectively. The yields of the spinach treated with the 4000 times diluted VdAL and the 6000 times diluted VdAL are improved by −7.45% and 56.38%, respectively, which indicated that spinach treated with VdAL with a proper concentration can improve yield thereof.

Experiments prove that the biological agent of VdAL according to the present invention, wherein VdAL is an active ingredient, can improve the quality of plant product and promote the fruit maturity.

1. After VdAL treatment, the contents of main nutrients and trace elements in watermelon are increased, and the palatability is improved. After VdAL treatment, the Vc content is remarkably improved by 50.41%; the soluble sugar content is improved by 8.88%; the protein content of dry matters is improved by 14.2%, the protein content of fresh watermelon is improved by 0.62%, the dry matter content declines by 12.4%, and the coarse fiber content declines a little. After VdAL treatment, the masses of Ca, Cu. Fe, K, Mg, Mn, Na, P and Zn in each liter of fresh watermelon are increased by 12.75%, 16.54%, 19.21%, 16.46%, 1.05%, 20.45%, 2.13%, 10.02% and 19.73%, respectively; and the mass contents of Cu, Fe, K, Mn and Zn in fresh watermelon are increased by 2.09%, 19.09%, 1.88%, 5.72% and 5.07%, respectively.

2. After VdAL treatment, the cotton yield before first frost and the ginning outturn are increased. When Lu No. 30 is treated with the 3000 times diluted VdAL, the cotton yield before first frost is improved by 19.48%; when being treated with the 5000 times diluted VdAL, the cotton yield of Lu No. 30 before first frost is improved by 21.25%, the cotton yield of 616 before first frost is improved by 19.06%, and the cotton yield of Lu No. 25 before first frost is improved by 16.37%. When being treated with the 3000 times diluted VdAL, the ginning outturn is increased by 0.24%; and when being treated with the 5000 times diluted VdAL, the ginning outturn is increased by 0.49%.

3. After grape is treated with the 3000 times diluted VdAL, the Vc content of the grape is improved by 50.4%, the grape is brighter in color, grape clusters are compact and unlikely to drop and the mature time of the grape is 5 days ahead of time.

4. After cherries are treated with the 5000 times diluted VdAL, the mature time of the cherries is 5 days ahead of time, and the yield is improved by 28.28%.

5. The brittleness and sweetness of can-like radish treated with the 5000 times diluted VdAL are improved, which indicates that the can-like radish treated with VdAL, has strong palatability.

Experiments prove that the biological agent of VdAL according to the present invention, wherein VdAL is an active ingredient, can improve the drought resistance of plant:

The plant treated with a solution having VdAL mass percentage concentration of 1-2% all die on the 15-20$^{th}$ day of water control, the plant not treated with VdAL all die on the 10-12$^{th}$ day of water control, and the dead time of the plant treated with the solution having VdAL mass percentage concentration of 1-2% is obviously longer than that of the plant not treated with VdAL. According to the re-watering treatment on the plant treated with a solution having VdAL mass percentage concentration of 0.2-2% after watering is stopped, the chlorophyll content of plant treated with VdAL is 34.5-34.4 SPAD, which is remarkably higher than that of plant not treated with VdAL; and the re-watering index of plant treated with VdAL is 0.43-0.52, which is remarkably higher than that of plant not treated with VdAL. It indicates that VdAL having a proper concentration can improve the drought resistance of wheat.

Experiments prove that the biological agent of VdAL according to the present invention, wherein VdAL is an active ingredient, can promote coloration of plant fruit:

1. The color of cherry treated with the 5000 times diluted VdAL is significantly redder than that of untreated cherry, which indicated that VdAL can promote coloration of cherry.

2. After grape is treated with the 3000 times diluted VdAL, the color of grape is brighter.

Experiments prove that protein VdAL and the biological agent thereof in the present invention can promote plant growth, improve the yield of plant, improve quality of plant product and palatability of plant fruit, improve the drought resistance of plant, promote coloration of plant fruit, and promote t fruit maturity.

The invention claimed is:

1. A method of treating a plant with a biological agent, the method comprises applying a biological agent to a plant, wherein said biological agent comprises a protein comprising the amino acid sequence as set forth in SEQ ID NO: 1, wherein said protein has VdAL protein activity in said biological agent, and wherein said application of said biological agent to the plant increases plant yield, increases plant growth, improves plant product quality, improves drought resistance or promotes fruit coloration of said treated plant as compared to a control plant of the same species that is not treated with said biological agent and is grown under identical conditions.

2. The method of claim 1, wherein said protein is a fusion protein comprising a labeled peptide tag at N-terminal or C-terminal end of said protein as set forth in SEQ ID NO: 1, and wherein said fusion protein has VdAL protein activity of said SEQ ID NO: 1.

3. The method according to claim 1, wherein said plant is a plant of dicotyledoneae or monocotyledonae.

4. The method according to claim 1, wherein said plant growth is vegetative growth and/or reproductive growth.

5. The method according to claim 1, wherein said plant product quality is nutrient content or trace elements.

* * * * *

SEQUENCE LISTING

```
<160> NUMBER OF SEQ ID NOS: 7

<210> SEQ ID NO 1
<211> LENGTH: 297
<212> TYPE: PRT
<213> ORGANISM: Artificial sequence
<220> FEATURE:
<223> OTHER INFORMATION: VdAL protein

<400> SEQUENCE: 1

Met Leu Ser Leu Gln Thr Ala Ala Leu Leu Leu Phe Pro Leu Val Ala
1               5                   10                  15

Ala Ser Pro Val Ala Arg Ala Ala Glu Thr Ser Val Thr Val Thr Val
                20                  25                  30

Asp Thr Ala Pro Ala Gly Pro Thr Ser Ser Thr Tyr Asn Trp Ala Glu
            35                  40                  45

Gly Trp Lys Ala Asn Phe Pro Ile His Gln Ser Cys Asn Ile Thr Leu
        50                  55                  60

Arg Thr Gln Leu Glu Ala Ala Leu Ala Glu Thr Met Thr Ile Ala Ala
65                  70                  75                  80

His Ala Arg Asp His Leu Leu His Asn Pro Lys Ser Glu Leu Ala Thr
                85                  90                  95

Lys Phe Phe Gly Asn Gln Ser Val Ala Gly Pro Ile Gly Trp Tyr Ser
                100                 105                 110

Lys Val Val Ser Thr Asp Lys Ser Glu Met Leu Phe Arg Cys Asp Asp
            115                 120                 125
```

```
Pro Asp Arg Asn Cys Ala Thr Gln Asp Gly Trp Ala Gly His Trp Arg
    130                 135                 140
Gly Ser Asn Ala Thr Gln Glu Thr Val Ile Cys Asp Leu Ser Tyr Glu
145                 150                 155                 160
Ile Arg Arg Pro Leu Ala Ala Leu Cys Gly Gly Tyr Thr Val Ala
                165                 170                 175
Glu Ser Lys Leu Asn Thr Tyr Trp Ala Thr Asp Leu Leu His Arg Ala
            180                 185                 190
Phe His Leu Pro Gly Ile Ser Asp Gly Ile Ile Asp His Tyr Ala Glu
                195                 200                 205
Asp Tyr Ala Glu Ala Leu Lys Leu Ala Ala Thr Glu Pro Glu Leu Ser
    210                 215                 220
Ile Ile Asp Ser Asp Thr Leu Gln Tyr Phe Ala Ile Glu Ala Tyr Ala
225                 230                 235                 240
Tyr Asp Ile Ala Ile Pro Gly Val Gly Cys Pro Gly Glu Lys Pro Ile
                245                 250                 255
Ile Asp Thr Ala Ala Gly Thr Ser Thr Ala Ala Pro Thr Thr Thr Thr
            260                 265                 270
Ala Ser Asp Ala Ser Gly Thr Thr Thr Ala Asn Ala Ser Cys His Thr
    275                 280                 285
His Asp Asp Gly Phe Val His Cys Ser
    290                 295
```

<210> SEQ ID NO 2
<211> LENGTH: 894
<212> TYPE: DNA
<213> ORGANISM: Artificial sequence
<220> FEATURE:
<223> OTHER INFORMATION: VdAL gene

<400> SEQUENCE: 2

```
atgctttctc tccagaccgc agccctgctg ctcttccctc tcgtcgctgc ctctcccgtg      60
gcacgcgctg ctgagaccag tgttaccgtc acggtggaca ctgcccctgc cggccctacc     120
agctccacct acaactgggc cgaaggctgg aaggccaact ccccatcca ccagtcttgc      180
aacatcaccc ttcgtactca gctcgaggct gctctcgccg agaccatgac cattgcggcc     240
cacgcccgcg atcatcttct ccacaacccc aagtccgagc tggcgacgaa gttcttcggc     300
aaccagtctg tcgccggccc catcggctgg tactccaagg tcgtctcgac cgacaagtct     360
gagatgctct ccgctgcga cgaccctgat cgtaactgcg ctacccaaga tggctgggcc     420
ggccactggc gcggctcgaa tgccacccag gagacggtca tctgcgacct ctcctacgag     480
atccgccgcc tcttgccgc tctctgcggt ggtggttata ccgtggccga gtccaagctc     540
aacacctact gggccactga ccttctgcac cgcgccttcc acctgcccgg catcagcgac     600
ggcatcatcg atcactacgc tgaggattac gccgaggccc tcaagcttgc cgccactgag     660
cctgaactct ccatcatcga cagcgacacc cttcagtact cgccattga ggcttatgcc      720
tatgacattg ccatccccgg cgtcggctgc cccggcgaga agcccatcat tgacaccgcc     780
gccggcacca gcaccgctgc cccgactact actaccgcca gcgatgccag cggcaccacc     840
accgccaatg cttcgtgcca cacccacgac gatggctttg ttcactgctc gtag           894
```

<210> SEQ ID NO 3
<211> LENGTH: 5
<212> TYPE: PRT
<213> ORGANISM: Artificial sequence
<220> FEATURE:

-continued

```
<223> OTHER INFORMATION: Poly-Arg

<400> SEQUENCE: 3

Arg Arg Arg Arg Arg
1               5

<210> SEQ ID NO 4
<211> LENGTH: 6
<212> TYPE: PRT
<213> ORGANISM: Artificial sequence
<220> FEATURE:
<223> OTHER INFORMATION: Poly-His

<400> SEQUENCE: 4

His His His His His His
1               5

<210> SEQ ID NO 5
<211> LENGTH: 8
<212> TYPE: PRT
<213> ORGANISM: Artificial sequence
<220> FEATURE:
<223> OTHER INFORMATION: FLAG

<400> SEQUENCE: 5

Asp Tyr Lys Asp Asp Asp Asp Lys
1               5

<210> SEQ ID NO 6
<211> LENGTH: 8
<212> TYPE: PRT
<213> ORGANISM: Artificial sequence
<220> FEATURE:
<223> OTHER INFORMATION: Strep-tag II

<400> SEQUENCE: 6

Trp Ser His Pro Gln Phe Glu Lys
1               5

<210> SEQ ID NO 7
<211> LENGTH: 10
<212> TYPE: PRT
<213> ORGANISM: Artificial sequence
<220> FEATURE:
<223> OTHER INFORMATION: c-myc(non)

<400> SEQUENCE: 7

Glu Gln Lys Leu Ile Ser Glu Glu Asp Leu
1               5                   10
```